(12) United States Patent
Mark

(10) Patent No.: US 9,760,682 B2
(45) Date of Patent: Sep. 12, 2017

(54) WORKFLOW AND RESOURCE MANAGEMENT SYSTEM WITH INTEGRATED BI-DIRECTIONAL COMMUNICATIONS

(75) Inventor: Jacob Mark, Needham, MA (US)

(73) Assignee: HINSIGHT-MOBILE HEARTBEAT HOLDINGS, LLC, Nashville, TN (US)

( * ) Notice: Subject to any disclaimer, the term of this patent is extended or adjusted under 35 U.S.C. 154(b) by 0 days.

(21) Appl. No.: 13/027,158

(22) Filed: Feb. 14, 2011

(65) Prior Publication Data

US 2012/0042039 A1    Feb. 16, 2012

Related U.S. Application Data

(60) Provisional application No. 61/304,250, filed on Feb. 12, 2010.

(51) Int. Cl.
*G06F 19/00* (2011.01)
(52) U.S. Cl.
CPC .......... *G06F 19/327* (2013.01); *G06F 19/345* (2013.01); *G06F 19/322* (2013.01)
(58) Field of Classification Search
CPC .............. H04L 29/08558; H04L 67/12; H04L 2209/88; H04L 45/00; H04W 40/24; H04W 4/005
USPC .......... 709/206, 224–238; 705/3–4; 715/780; 368/70, 82, 107–109, 187–263; 600/300
See application file for complete search history.

(56) References Cited

U.S. PATENT DOCUMENTS

| | | |
|---|---|---|
| 4,935,962 A | 6/1990 | Austin |
| 6,549,625 B1 | 4/2003 | Rautila et al. |
| 6,728,378 B2 | 4/2004 | Garib |
| 7,092,370 B2 | 8/2006 | Jiang et al. |
| 8,326,651 B2 | 12/2012 | McLaren et al. |

(Continued)

FOREIGN PATENT DOCUMENTS

EP    0 328 232    8/1989

OTHER PUBLICATIONS

OpenScape for SAP Business by Design, Siemens, Siemens Enterprise Communications Inc., 2010.
Syclo Teams With SAP to Deliver Mobile Asset and Service Management Solutions Leading Software Providers Co-Innovate to Deliver Mobile Asset Management and Field Service Applications for SAP Customers Worldwide, SAP AG, 2009.
Mobile Heartbeat, Retail Heartbeat Limited.

(Continued)

*Primary Examiner* — Andrew Lai
*Assistant Examiner* — Chuong M Nguyen
(74) *Attorney, Agent, or Firm* — Kilpatrick Townsend & Stockton LLP

(57) ABSTRACT

A system for controlling process pathways. The system includes a network, a system backend communicable with said network comprising a processor configured to generate a process pathway based on a predefined set of rules reflecting a predetermined condition, and a series of notifications corresponding to the process pathway, a mobile device communicable with said system backend via said network, the mobile device being configured to receive from said backend at least one notification, of said series of notifications, the notification defining a task of the process pathway, and upon which notification a user is authorized to act, allowing the user to modify a state of said the notification with a one-step action, the mobile device further communicating the modified state of the at least one notification to the system backend over said network and wherein said modified state of the notification causes said processor to effect a change to said process pathway.

33 Claims, 14 Drawing Sheets

(56) References Cited

U.S. PATENT DOCUMENTS

| | | |
|---|---|---|
| 2001/0005839 A1 | 6/2001 | Maenpaa et al. |
| 2001/0044786 A1 | 11/2001 | Ishibashi |
| 2005/0165914 A1 | 7/2005 | Moore et al. |
| 2006/0053035 A1 | 3/2006 | Eisenberg |
| 2006/0100909 A1 | 5/2006 | Glimp et al. |
| 2006/0143041 A1* | 6/2006 | Tipirneni .............. G06F 19/322 705/2 |
| 2006/0282302 A1* | 12/2006 | Hussain ................ G06F 19/327 705/2 |
| 2007/0254636 A1 | 11/2007 | Jiang |
| 2007/0254684 A1 | 11/2007 | Jiang |
| 2009/0300170 A1* | 12/2009 | Bhame ................... H04L 45/00 709/224 |
| 2010/0286488 A1* | 11/2010 | Cohen ................... G06F 19/323 600/300 |
| 2010/0305970 A1 | 12/2010 | McLaren et al. |
| 2010/0305971 A1 | 12/2010 | McLaren et al. |
| 2010/0305972 A1 | 12/2010 | McLaren et al. |
| 2010/0306858 A1 | 12/2010 | McLaren et al. |

OTHER PUBLICATIONS

The Vocera Communications Badge, 2009, 3M, St. Paul, USA.
Results of Search in US Patent Collection db for: ((AN/SAP and mobile) and (collab$), USPTO Patent Full-Text and Image Database, Dec. 28, 2009.
Results of Search in US Patent Collection db for: (CCL/235/375 and workflow), USPTO Patent Full-Text and Image Database, Dec. 30, 2009.
Results of Search in US Patent Collection db for ((context-aware and mobile) and (calling or alert$)), USPTO Patent Full-Text and Image Database, Dec. 28, 2009.
Results of Search in US Patent Collection db for ((automat$ and workflow) and (healthcare)), USPTO Patent Full-Text and Image Database, Dec. 28, 2009.
Ray Hunt, PKI and Digital Certification Infrastructure, 2001, 234-239, 1531-2216/01, IEEE.
International Search Report and Written Opinion of PCT/US2011/024795 dated Apr. 6, 2011, all pages.
International Preliminary Report on Patentability of PCT/US2011/024795 dated Apr. 6, 2011, all pages.

* cited by examiner

NURSE CALLS AND VS EXCEPTIONS
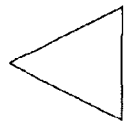
A TRIANGLE COULD HAVE SEVERAL INDICATORS. ALL ARE CONFIGURABLE AND HOSPITAL SPECIFIC. eg:
AI — ACUITY
VS! — VITAL SIGN EXCEPTION
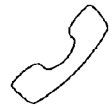
A PHONE ICON NEXT TO A PATIENT NAME INDICATES THAT THERE WAS A MESSAGE RELATED TO THAT PATIENT eg: SMS OR A NURSE CALL: NURSE
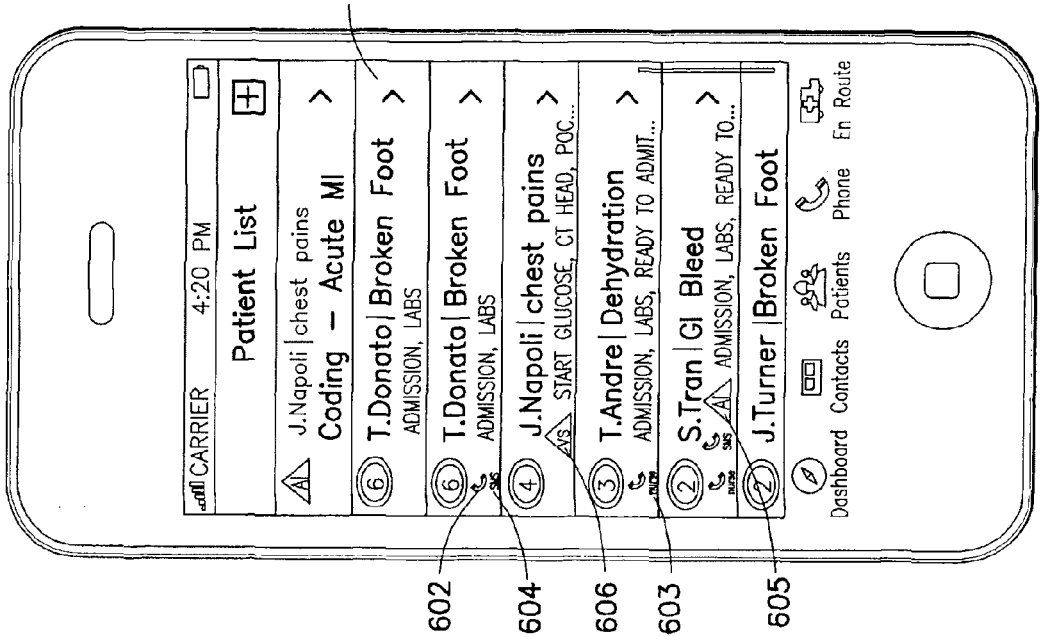
FIG.6

WORKFLOW AND RESOURCE MANAGEMENT SYSTEM WITH INTEGRATED BI-DIRECTIONAL COMMUNICATIONS

RELATED APPLICATIONS

This application claims priority from U.S. Provisional Patent Application No. 61/304,250 filed Feb. 12, 2010 incorporated by reference herein in its entirety.

BACKGROUND

1. Field

The present embodiments relates to a workflow and resource management system, more particularly, to a workflow and resource management system that utilizes data applications with integrated bi-directional communications.

2. Brief Description of Related Developments

Some work environments demand a great deal of coordination and communication between various members of a team or teams, as well as resource management. Some possible work environments may include, for instance, the administration and management of healthcare provided within a medical or healthcare environment. Other possible work environments may include a retail environment or any other environment that may require the coordination of resources and personnel. A system is needed in those environments that would allow for improved communication and coordination while simultaneously decreasing cost, increasing portability, increasing ease of use as well as the ability to audit problem areas. Such environments also require the ability to monitor possible problems and be flexible enough to adjust dynamically should such problems arise.

Many possible solutions have been created to address these problems. In hospitals, for instance, the use of beepers have been prevalent to contact doctors and other personnel. However, such a solution is largely ad hoc and lacks the means to integrate data with voice communications. It also lacks a central system that allows for optimized coordination of personnel and resources. Further, a pager-based system lacks the capability of tracking and auditing the performance of various actors within the system. Computing devices have also been used to help address some of these problems. Stationary terminals allow for users to communicate between various parties and also to access information regarding resources, records and any other information. However, stationary terminals lack portability and may hamper communication. Further, the availability of certain stationary terminals may limit their usefulness in the field. Notebook computers may also be used to solve the issue of portability. However, they are often bulky and may be difficult to use in constrained or otherwise limited environments. Further, battery life may be poor for notebook computers. Communication utilizing stationary and notebook computers, for example, in the form of email and or instant messaging, may also be less convenient for users.

Other possible solutions may include mobile computing devices, such as wireless personal digital assistants (PDAs) or smartphones or other small mobile devices. However, these system lack features that will include a data application users can access for information as well as integrated communications from within the data application. These features are especially important in circumstances where the organization or work environment may have many team members. Additionally, these systems do not include a means by which coordination between individuals, teams and resources are managed dynamically and can adjust to address these problems on the fly. As organizations become larger and more complicated, there is a need for a system that is capable of addressing all possible needs in such environments.

BRIEF DESCRIPTION OF THE DRAWINGS

The foregoing aspects and other features of the present invention are explained in the following description, taken in connection with the accompanying drawings, wherein:

FIG. 6 is an exemplary user interface illustrating a list of jobs (e.g. patients) within a system.

DETAILED DESCRIPTION OF THE EXEMPLARY EMBODIMENTS

Figure 1:
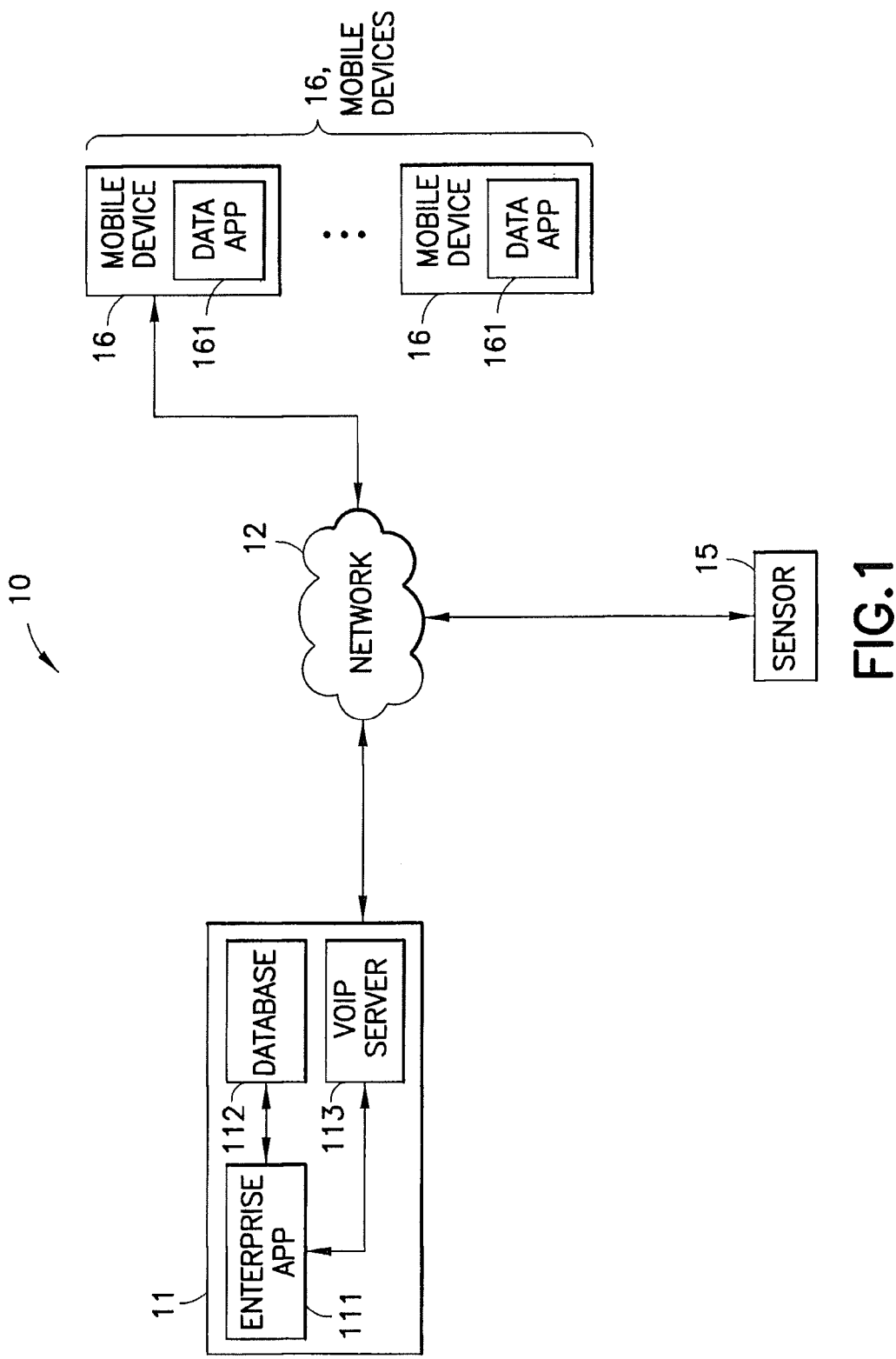
FIG. 1 is a schematic representation illustrating an overview of the one exemplary embodiment of a system incorporating features of the invention.

The disclosed embodiment is a, system for the management of process pathways within an organizational context. These organizational contexts may be, in a desired embodiment, a medical context. These may be, for example, hospitals, clinics, medical laboratories, or any other similar contexts related to healthcare. The following description may specifically refer to examples within a healthcare context, however, it is understood that the organizational context may relate to other organizational types, such as a retail context or other suitable workplace context. The disclosed embodiment relates to the real-time tracking and acceleration of workflow processes, or physical processes, of what may be referred to for purposes of description as jobs, for example patient care within a medical context, along with the actions of various team members within the system. Workflow processes to accomplish the job may be based on predefined rules. In a medical context, these rules may be in the form of defined procedures for treatment of a patient. Further, any such predefined rules may also take into consideration a further condition. For example, within a medical context, this may take the form of a patient's ailment or symptoms or any other suitable conditions that may influence how a patient may be treated. In alternate embodiments, the system may also use predefined rules and conditions in other contexts, such as retail, airports, hotels, construction sites or any other suitable context. The system may use these predefined rules, which may be similar to state machines, decision matrices, or decision trees, or any other suitable set of logical rules to generate workflow processes for a particular case. In alternate embodiments, these predefined rules may take any suitable form. In an exemplary embodiment, a process pathway for a job may take the form of, for instance, a series of task points or path points associated with the workflow or physical process, for instance, the treatment plan for a patient, or any other task in any other context. The series of task points or path points may, in an exemplary embodiment, correspond to a discrete physical task to be done in the furtherance of the job, for instance a specific step in the treatment of an patient in an emergency room. In alternate embodiments, a process pathway may take any other suitable form. The status of the process pathway, for instance, the state of the series of task points and whether a task point within is completed or not may, in on exemplary embodiment, provide a team member information associated with the status of the job, for instance, a patient as a patient goes through the system. When a process pathway is generated, the system may further generate a series of notifications based on the process pathway. These notifications may correspond, for instance, to specific task points or path points, or any other suitable type of notification. In an exemplary embodiment, the series of notifications may be generated by the system and sent to relevant individuals within the workflow. In another exemplary embodiment, the series of notifications may allow for team members to implement, in real time, or modify, in real time a work protocol. For instance, within a medical context, a patient's process pathway may be dynamically changed by for example a doctor, or administrator if it is determined that a different course of treatment may be necessary.

In an exemplary embodiment, the system may further have a system for communications. For example, system may allow for integrated communications within the system. For example, communications may take the form of multiple types—for instance, SMS, voice, voicemail, e-mail, instant messaging, or any other suitable means for communication. In an alternate embodiment, the system may use external communications means instead of integrated communications—for example, a data application may open an external application for communications means. In yet another alternate embodiment, communications may take any suitable form, or may not be present. Communications may be simplified for the user. In an exemplary embodiment, communications may allow for smart directories or smart dialing or smart communications selection. Such a simplified communications system may, in one exemplary embodiment, be invisible to users, wherein the system may select the most relevant individual or a group to contact for a relevant event or condition. In alternate embodiments, the communications system may take any suitable form including "push to talk", conferencing and broadcast voice.

The system may further have the means for auditing and quality control. Within an organizational context, quality assurance and quality control are necessary for operation, especially where the organizations are complex. This is especially true, for instance, in a healthcare context where the need for quality control may cause delays or harm to patient care. In one exemplary embodiment, the system may record, track and timestamp communications and actions and process pathways within the process pathway system. In alternate embodiments, any other means for auditing and quality control may be implemented within the system. Such quality control may also allow for the generation of reports or other reporting means to allow users to see delays, communications and errors. Such quality control means may be used for improved productivity, and may further improve the running of the system. Quality control, in other embodiments, may also be important to ensure proper actions in particularly serious situations or events. For example, within a medical context, this could mean for the treatment of stroke, chest pain, pneumonia or other immediately at risk patients. Further, auditing and quality control may be used to identify shortfalls within resources, personnel and other problems that may arise.

FIG. 1 illustrates a block diagram illustrating a workflow and resource management system in accordance with an exemplary embodiment. Although the present invention will be described with reference to the embodiment shown in the drawings, it should be understood that the present exemplary embodiments can be used individually or in any suitable combination thereof. It should also be understood that the forgoing description is only illustrative of the embodiments. Various alternatives and modifications can be devised by those skilled in the art without departing from the embodiments. Accordingly, the present embodiments are intended to embrace all such alternatives, modifications and variances.

Referring to FIG. 1, a system 10 having a backend 11 is depicted, the backend 11 may be the form of a general purpose computer system or server system. In alternate embodiments, the backend may also be multiple computers or servers or any other suitable device. Furthermore, backend 11 may be able to communicate over a network 12 with mobile devices that also communicate over network 12. In one embodiment, the network 12 may be a wireless network. The wireless network preferably is an 802.11 network, but may also be Bluetooth, GSM, CDMA, RF or any other suitable form of communication. In another embodiment, the network 12 may also be a wired network. Through the network 12, the backend 11 may be able to enable a variety of data communication technology, for example, but not limited to voice-over-IP, video-over-IP, text messaging, public switched telephone networks, or any other form of bi-directional communication. This may take the form of, for example, a voice over IP telephony server 113. The backend may also run an enterprise application 111 within a server environment. The enterprise application 111 may be implemented using a computer code comprising instructions that may be executed by a processor within the backend 11. The code may be embodied in a computer-readable medium such as a magnetic or optical disk, programmable memory chip, or any other non-transitory computer-readable medium. The enterprise application may communicate with a database 112 and access and update the information within the database. The enterprise application 111 acts as the controller for the workplace and resource system. The server environment upon which the enterprise application 111 runs may take the form of, for example, Java servlets, or any other suitable environment upon which an enterprise application may execute.

Referring again to FIG. 1, a number of mobile devices 16 may communicate over the network 12. As described previously, the network 12 may be a wireless network in some embodiments. The wireless network preferably is an 802.11 network, but may also be Bluetooth, GSM, RF, CDMA or any other suitable form of network. In other embodiments, the network 12 may also be a wired network. The mobile devices may, by means of a mobile data application 161, communicate with backend 11, for example via Web Services such as SOAP protocols, or any other suitable communications protocols and is capable of accessing and updating data stored within the database 112. The mobile data application 161 may take the form of a native application designed to run as computer code executed by data device 16. The computer code may be embodied in a computer-readable medium stored on data device 16 such as magnetic or optical disk, programmable computer chip or any other non-transitory computer-readable medium. In other embodiments, the mobile data application 161 may also take the form of a non-native application, for example, a Java-based application running on a virtual machine or a web-based application such as an HTML5 application. In some embodiments, the mobile devices may take the form of smartphones. For example, the mobile devices may utilize any platform, including iOS (iPad, iPhones, etc), Symbian (Nokia), Android devices (tablets, phones, etc), webOS devices, Windows 7 devices, Blackberries, etc. In other embodiments, the mobile devices 16 may also be in the form of Personal Digital Assistants (PDAs), computer terminals, or any other suitable device capable of running the mobile data application 161 described above. Generally speaking, the system may be platform agnostic and may accommodate any other suitable devices. Other devices may also be able to communicate with backend 11 through the network 12 as described above. Such devices may include sensors 15 or laboratory equipment, or any other suitable devices.

Figure 2:
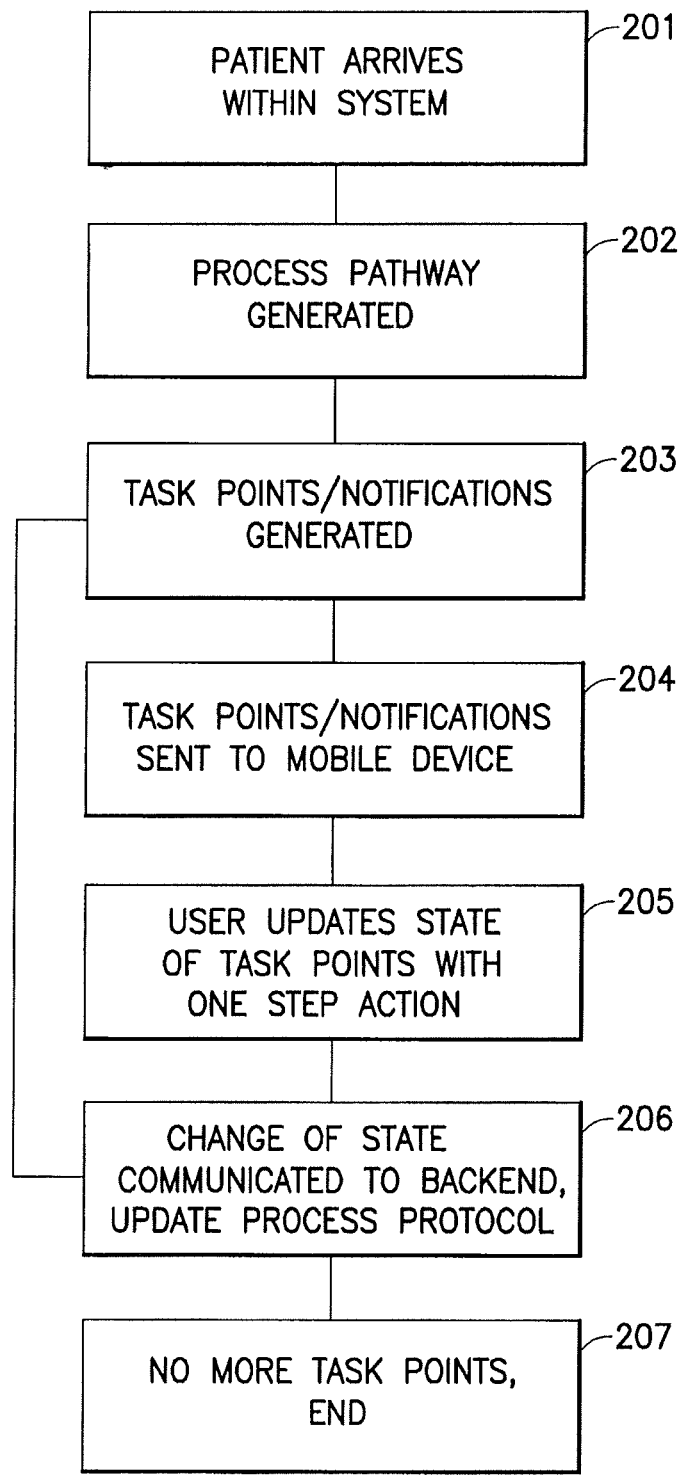
FIG. 2 is an exemplary flow diagram illustrating an exemplary embodiment of the process pathway generation system.

Referring now to FIG. 2, an exemplary flow diagram is shown detailing an exemplary embodiment of a process pathway system for a job within the work system. Generally, a process pathway system allows for simple action management that can connect all teams involved in every stage of a process pathway. Within a medical context, this may mean connecting all teams involved in every stage of a patient's care, from admittance, to surgery, departmental movements, discharge and beyond. The process pathway processing system may also allow for all teams to know in real time what has been done, what still needs to be done and by who, and when key things must happen in order to create and deliver best outcomes. A process pathway begins block 201, as a job is created and initiated, for example, a patient arrives within a system. In alternate embodiments, job creation and its initiation may occur in any other desired manner. A process pathway may be generated based upon predefined rules, block 202, within the system. The generation of a process pathway may be, in an exemplary embodiment, performed by the enterprise application 111 as seen in FIG. 1. In alternate embodiments, the generation of a process pathway may be performed elsewhere and be sent to the enterprise application 111, or any combination of generation by an enterprise application 111 and elsewhere. In yet alternate embodiments, the means for generating a process pathway by enterprise application or by any other means may further allow alteration of the process pathway, for example seen in FIG. 11. The job creation and initiation, 201, and the corresponding pathway generation may occur at the enterprise application 111 (see also FIG. 1) of the system. In an exemplary embodiment, the predefined rules within a system may be rules for determining a sequence of tasks for a particular process pathway. These predefined rules may further be conditioned on a predetermined condition. For example, in a healthcare context, the predefined rules may be procedures for treating an incoming patient within a hospital or clinic. The predetermined condition may, in the previous example, consist of a patient's condition or complaint or status. In alternate embodiments, any sort of predetermined rules or predetermined conditions may be used. In yet other alternate embodiments, the system may determine a process pathway automatically. For instance, the entry of a patient in a medical context may automatically generate a process pathway. In alternate embodiments, the generation of a process pathway may allow for further user access to allow for customization of a process pathway for a job. In yet other alternate embodiments, a user may take anywhere from total to nominal amounts of control in the generation of a process pathway.

Figure 3:
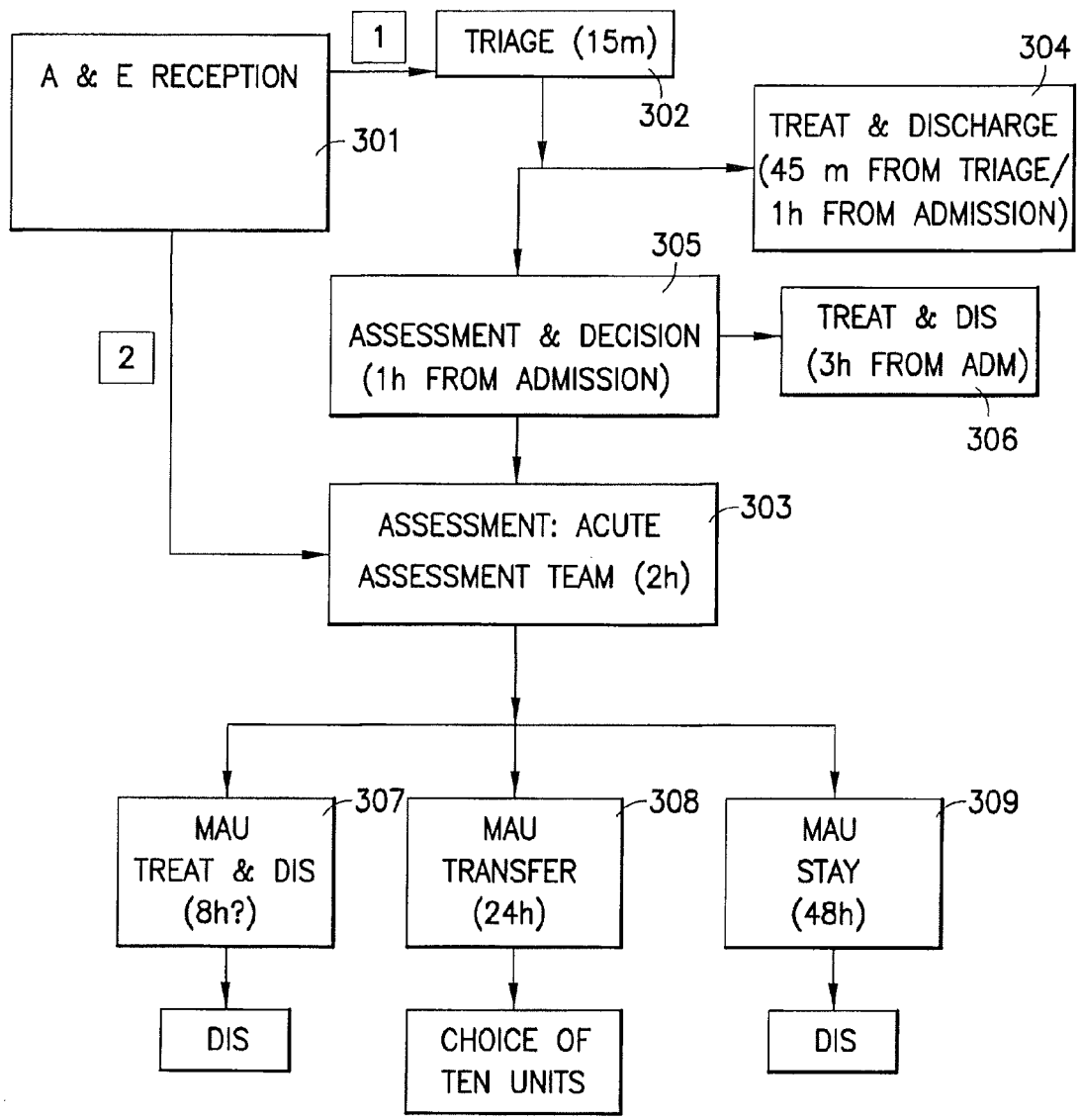
FIG. 3 is an exemplary flow diagram illustrating a possible set of rules and procedures used in a process pathway generation system.

Referring now to FIG. 3, an exemplary embodiment of a set of predefined rules may be seen in the form of a flow chart. FIG. 3 illustrates the procedure within an Emergency Department in a hospital for the treatment of incoming patients. In alternate embodiments, predefined rules may take any suitable form, for example in the form of decision matrices, decision trees or any other suitable form of procedural formats. Within the medical context, treatment using the procedure illustrated in FIG. 3 may be further based on a condition such as, for example, the status or condition of a patient. For example, a determination that a patient's condition is not serious may result in the patient being sent from reception 301 to triage 302. At triage, a further determination of the patient's condition may determine whether the patient is treated and discharged 304 or whether further assessment and decision is warranted 305. If further assessment and decision 305 makes a determination that the patient's condition is not serious, the patient can be treated and discharged 306 or, if the condition is determined to be serious or warranting of the additional assessment, the patient may be sent to the Acute Assessment Team 303 where the patient may be further sent to additional units for inspection or observation or treatment 307, 308, 309. The procedure illustrated in FIG. 3 demonstrates an exemplary set of rules for the performance of a job such as the treatment of a patient within an Emergency Room department. In alternate embodiments, any other form of rules may be used in any other suitable form within the context of performing a job.

Referring again to FIG. 2, after a process pathway is generated 202 according to predefined rules and reflecting a predetermined condition, the system may further generate a series of task points corresponding to the generated process pathway 203. The task points generated in 203 may take the form of, in some embodiments, notifications, or path points or tasks. These task points or notifications may be generated by the enterprise application 111 as seen in FIG. 1 in an exemplary embodiment. In alternate exemplary embodiments, these may be generated elsewhere and then fed into the enterprise application 111. In yet alternate embodiments, the task points or notifications may be generated by any suitable means, including any suitable combination of being generated by the enterprise application 111 or being generated elsewhere. The task points generated in 203 may be sent over a communications network to, in one exemplary embodiment, mobile devices 16 via a network. For example, a notification(s corresponding to and representative of the task point, that may include suitable information identifying the task point, may be sent to the mobile device 16. The system may, in an exemplary embodiment, send only a portion of the task points, or notification corresponding thereto, generated in 203 to a mobile device 16 (see 204). The portion of the task points generated in 203 may, in an exemplary embodiment, represent those task points relevant to a particular team member using the mobile device 16. For example, if a process pathway generated for an accident victim includes CAT scans and X-Rays, the system may send a task point to the CAT department for the victim corresponding to the patient's CAT scan and another task point to the X-Ray department for the patient's X-Ray task because they are relevant to each department. In alternate embodiments, the system may assign task points to specific team members. For example, a task point for laboratory tests may be assigned to a specific laboratory technician rather than to just the laboratory department. The system may, in an exemplary embodiment, assign task points to specific team members based upon roles they have. For example, a task point for surgery may be assigned to one or more surgeons, however the same task point may not be assigned to a laboratory technician. In alternate embodiments, the system may assign task points based on additional factors, including, but not limited to, scheduling considerations, availability, work load, or any other suitable factors that may affect the ability of a team member to perform an assigned task point. In alternate embodiments, the system may also send all task points or representative communications thereof, for a patient to a mobile device 16. A user with a mobile device 16 may be able to modify the state of any task points or their representative communications sent in 204 (see 205). In one exemplary embodiment, the user with a mobile device 16 may be able, for instance, to effect a change to the state of a task point between complete or incomplete or between off and on. In alternate embodiments, the user with a mobile device may further be able to change the state of a task point to other states, such as, in a non-limiting example, delay states. In an exemplary embodiment, the user may effect the change in task point state in 205 in a one-step action. This may, for instance, be the form of a single click, or a toggle or any other suitable one-step action. In alternate embodiments, any suitable means of effecting the change in task point state may be used. The change of state for a task in 205 may be communicated to the system backend 11 via the network from the mobile device 16 (see 206). In 207, the system backend may receive the change of state for a task point from the mobile device 16 and effect a change to the process pathway generated in step 202. In an exemplary embodiment, the change effected on a process pathway may be an indication of completion of non-completion of a particular task point. In alternate embodiments, the process pathway may be dynamically altered based on the change effected upon the process pathway. This may be, in a medical context, a change with a patient's treatment option. These changes in task point states may allow users to create or alter process pathways on the fly. At 207, when no task points remain uncompleted, the process pathway may terminate for that particular task. In alternate embodiments, task points generated may also have additional data, for example, status priority data. In yet alternate embodiments, task points may also have data indicating time frames for performance or completion of the task point. For example, this may include deadlines for certain tasks to be completed. In alternate embodiments, any suitable additional information may be available.

In alternate embodiments, task or representative notification thereof, points may also be used to alert users to, for example, incomplete task points, or changes in states for task points, upcoming task points, or any other suitable alerts. These task points, may, for instance, have time window data, in some instances, or any other suitable additional information. In the example of alerts for upcoming task points, for instance, an exemplary embodiment of the alert may include the alert being generated when the time window information for a task point may be within a certain threshold. In the example of a delayed task, the alert may be generated if the time has exceeded the time window information for a task point by a certain threshold. In alternate embodiments, any other suitable types of alerts and methods for generating said alerts may also be used.

Figure 2A:
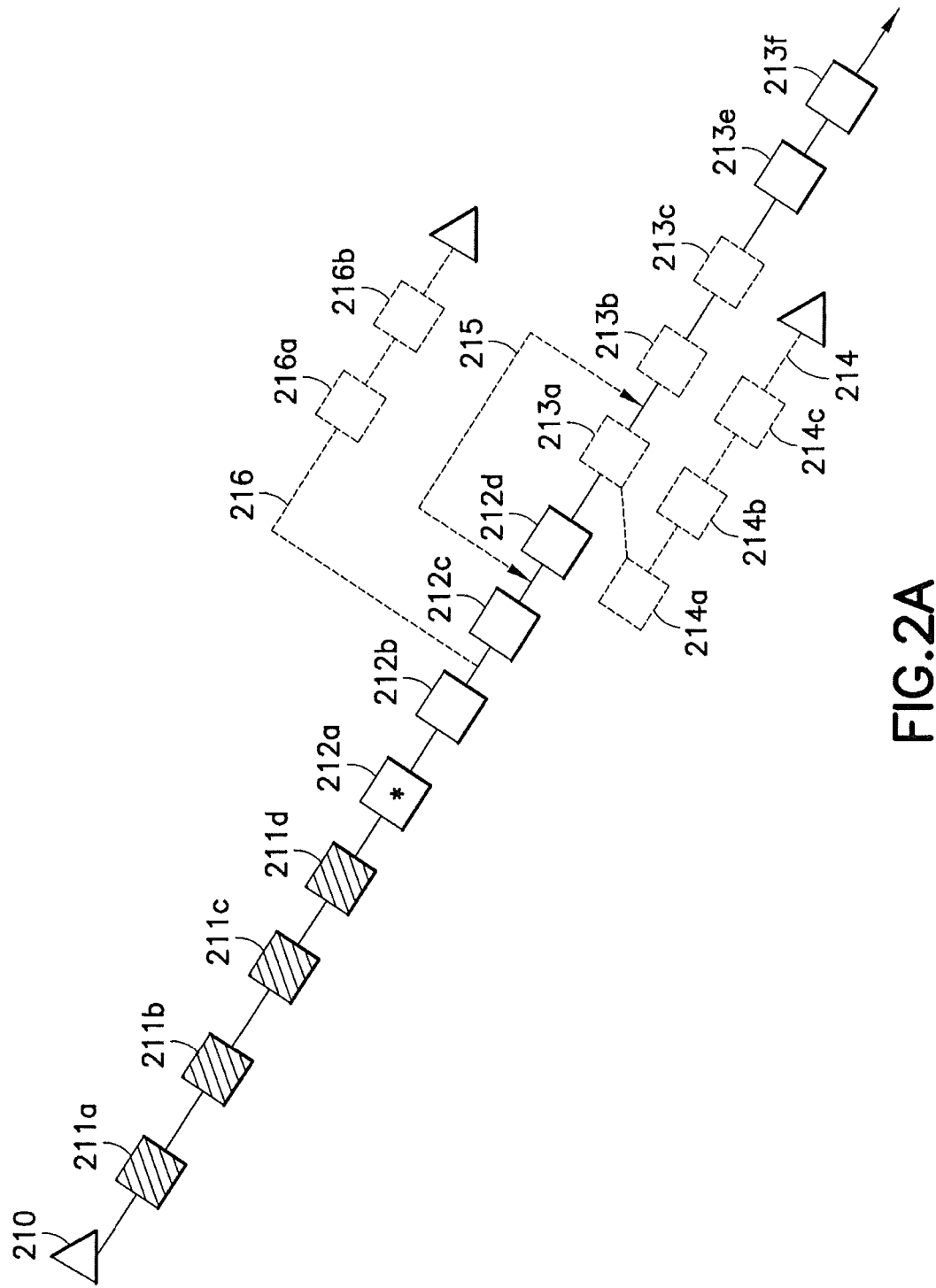
FIG. 2A is an exemplary diagram of an exemplary process pathway.

Referring now to FIG. 2A, an exemplary illustration of task points according to an exemplary process pathway is shown. The series begins at 210, represented by the triangle which may, for instance, represent the beginning of a series of task points for the exemplary job process pathway. Within a healthcare provider, for instance, this may represent the admittance of a patient. In alternate embodiments, it may represent simply the generation of the process pathway for the job, by the system according to a predefined set of rules and a predefined, or any other suitable start point for a series of task points. In yet other embodiments, the beginning 210 of the series of task points may be purely conceptual and not part of any implementation. The series of task points may, for instance include various types of task points. Task points 211*a*-211*d*, for instance, are represented by darkened shaded boxes within the exemplary illustration. These may, in this exemplary embodiment, represent task points that may have been already completed—i.e. the state of the task point was changed to complete by, for example, a user or any other suitable means. Other task points within the series of task points within this exemplary embodiment may be seen by task points 212*a*-212*d* and 212*e*-212*f*. These are, within the exemplary illustration, represented by unshaded boxes. These represent task points that may, in this exemplary embodiment, that are not yet complete—i.e. the state of the task point was not toggled to complete and must still be done, or any other suitable task point not yet finished. In some of the incomplete task points or their representative notification(s) 212*a*-212*d*, 212*e*-212*f*, additional data may be seen or otherwise made suitable on the mobile device 16 (see also FIG. 4). For example, 212*a* is an incomplete task point that may contain additional information, for example visible on the display of the mobile device 16, as represented by the presence of an asterisk within the unshaded box. In an exemplary embodiment, for instance, the additional information may be information regarding delay or past-due task point. In alternate embodiments, the additional information could take on any suitable form, including alerts or status or any other information associated with a task point. Potential or possible task points 213*a*-213*c* and representative notifications therefrom, may also be represented. These may be, for instance, task points generated by the process pathway that may be activated in the future (such as will be described further below), or are potential possible task points that may occur in an exemplary embodiment. These potential task points may be activated in the future, in an exemplary embodiment, by a user or by the system backend. In an exemplary embodiment, activation (i.e. changing the state of a task point and/or its representing notification from inactive to active) of a potential task points 213*a* may lead to future potential task points 213*b* (that may be based or dependent on another task point 213). In alternate embodiments, activation of a potential task point 213*a* may lead to the creation of a new potential series of task points 214. In yet alternate embodiments, any other suitable consequence of the activation of a potential task point with regards to the process pathway may be possible. Conversely, as may be realized, the task point state may be changed to deactivate an active task point, with the corresponding closing of the task point, and any desired associated task points. State change of task point to active or deactivate may be effected in a similar manner as will be described further below.

Other changes to the task point(s) or task point series representing the process pathway may also be possible. For instance, the potential branch of the task point series 216 may represent where the task points have been altered to reflect an altered process pathway. This may be done, in an exemplary embodiment, by the backend for any suitable reason in order to generate a desired process pathway, or in alternate embodiments, may be done by any other suitable means. Path 215 may represent that the satisfaction of potential bypasses for certain task points. For example, in an exemplary embodiment, the completion of a task point 212c may bypass task points 212d and 213a that may no longer be desired. In alternate embodiments, the completion of a task point may also generate a path 215 back to an earlier task point within the series of task points. Upon generation of such, notification(s) representations of the task points may be sent to the mobile devices. In alternate embodiments, the exemplary path 215 may represent any suitable bypass paths within the series of task points.

Figure 4:
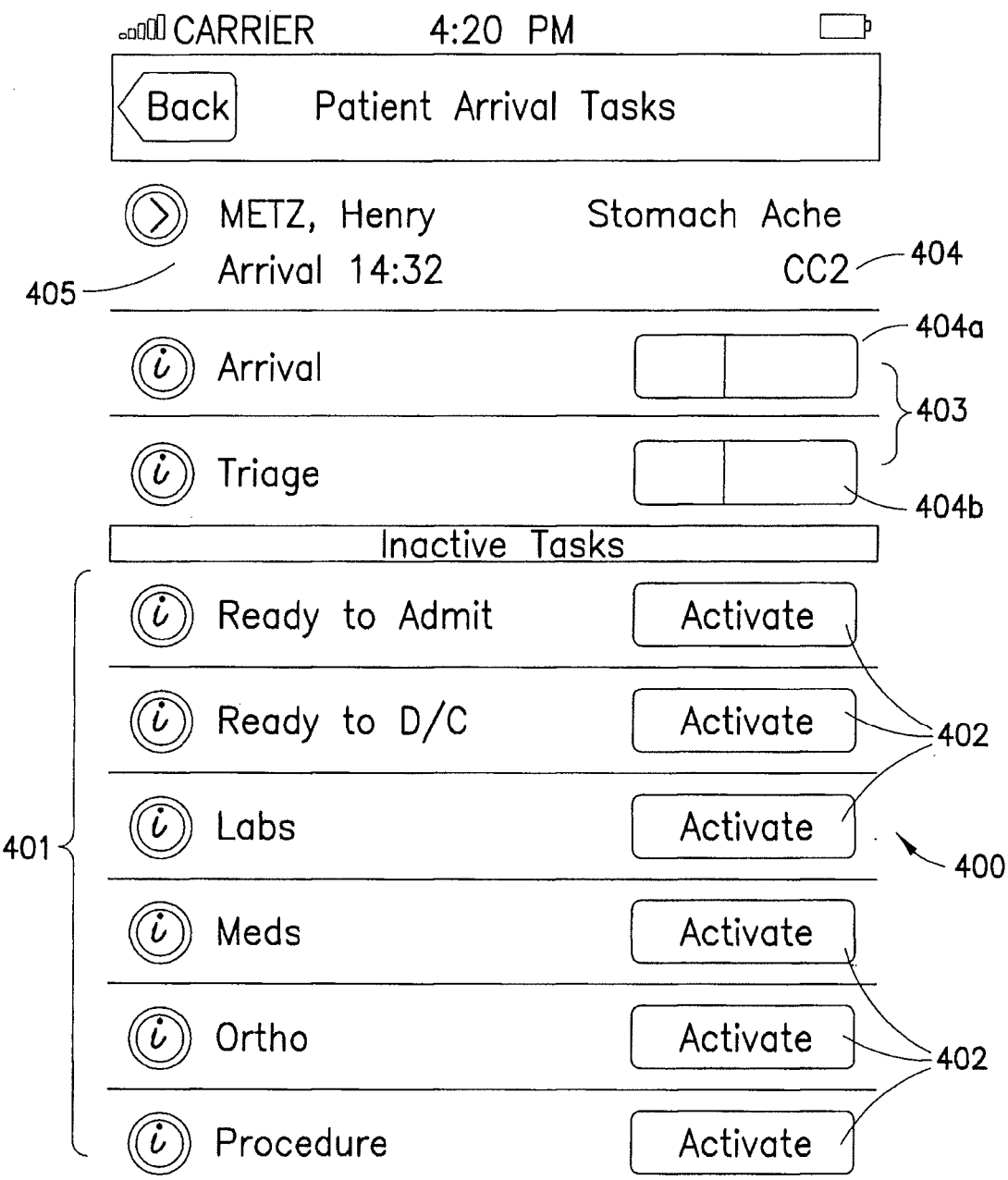
FIG. 4 is an exemplary user interface illustrating a notification list.

FIG. 4 shows an exemplary user interface for a mobile device 16 showing a exemplary set of representative notifications of task points associated with a process pathway as may appear. In this exemplary embodiment, the process pathway is for the treatment of a patient within a healthcare context. Patient information (more generally the job or process context information) 405 may be presented within the user interface 400. This may be, in an exemplary embodiment as shown in FIG. 4, the name of the patient along with information about time of arrival for the patient. The job context information 405 shown is merely exemplary, and in alternate embodiments may be shown in any suitable manner. In alternate embodiments, any information regarding a job (e.g. patient) may be presented, and is not limited to the information shown on FIG. 4. The user interface 400 may also contain information regarding a patient condition 404. In an exemplary embodiment, the condition may be, for instance, a patient's ailment or complaint or physical condition. In alternate embodiments, any condition regarding the job (e.g. patient) may be presented, or in other alternate embodiments, no information about condition may be present at all. Below the patient information 405 and patient condition information 404, a list of task points or representative notifications 403 may be presented in the exemplary embodiment illustrated in FIG. 4. The form of the notifications or task point shown in FIG. 4 are merely exemplary and in alternate embodiments the notifications or task points may be depicted on the user interface in any suitable manner including flags, icons, thumbnails) In an exemplary embodiment, the task points 403 presented may indicate a list of all expected tasks corresponding to a particular patient's process pathway. In the present exemplary embodiment, two task points are available: arrival 404a and triage 404b. In the exemplary embodiment, each task point 404a and 404b presents the user with an input or interface for effecting a change in state for the task point. In the current exemplary embodiment, this may be in the form of toggle switches upon a screen. In alternate embodiments, this may be a button, or a check box or any other suitable forms of modifying the state of a task point. In an exemplary embodiment, the input may take the form of one-step action input (e.g. one touch interface) for modifying the state of a task point. In alternate embodiments, any suitable means of modifying the state of a task point may be used. By allowing a user to modify the state of the task points 404a and 404b, the effected change in state of the task points 404a and 404b may be communicated to the backend where a corresponding change may be effected upon the process pathway as described previously and shown in FIG. 2a. In an exemplary embodiment, the state of the task points corresponding to a patient's process pathway may also, at a glance, present information on the current status of the patient's status as they are being treated. In the exemplary embodiment illustrated in FIG. 4, a list of possible future (currently inactive) task points 401 is also available for the user. In the exemplary embodiment, the user may be presented with options to activate 402 an inactive task point 401. In such a circumstance, for instance, the user may, for instance, alter the status of task points presented and may further alter the process pathway on the fly. For example, a doctor presented with the screen illustrated in FIG. 4 may determine that the patient's stomach ache may require further testing. In the exemplary embodiment, the doctor may select the "Activate" button (for example, 402) next to the inactive task point item for Labs (for example, 401). The corresponding change in state for the Labs task point may be effected. In an exemplary embodiment, the change in state for the task point may be communicated to a system backend wherein the process pathway generated for the patient may be correspondingly altered. In the example, an activation of a Labs task point may result in the process pathway for the patient to be altered to generate a changed or new process pathway wherein the patient may be further sent to a laboratory in furtherance of his treatment. In alternate embodiments, other suitable changes to the process pathway may also occur. In an exemplary embodiment, the change in the process pathway is dynamic and users may change the process pathway on the fly. Further, in the exemplary embodiment, the changes in state for a task point as shown in FIG. 4 may be in the form of a one-step action (e.g. one touch) for a user. In alternate embodiments, the change in state for a task point may be effected with any suitable means.

Figure 5:
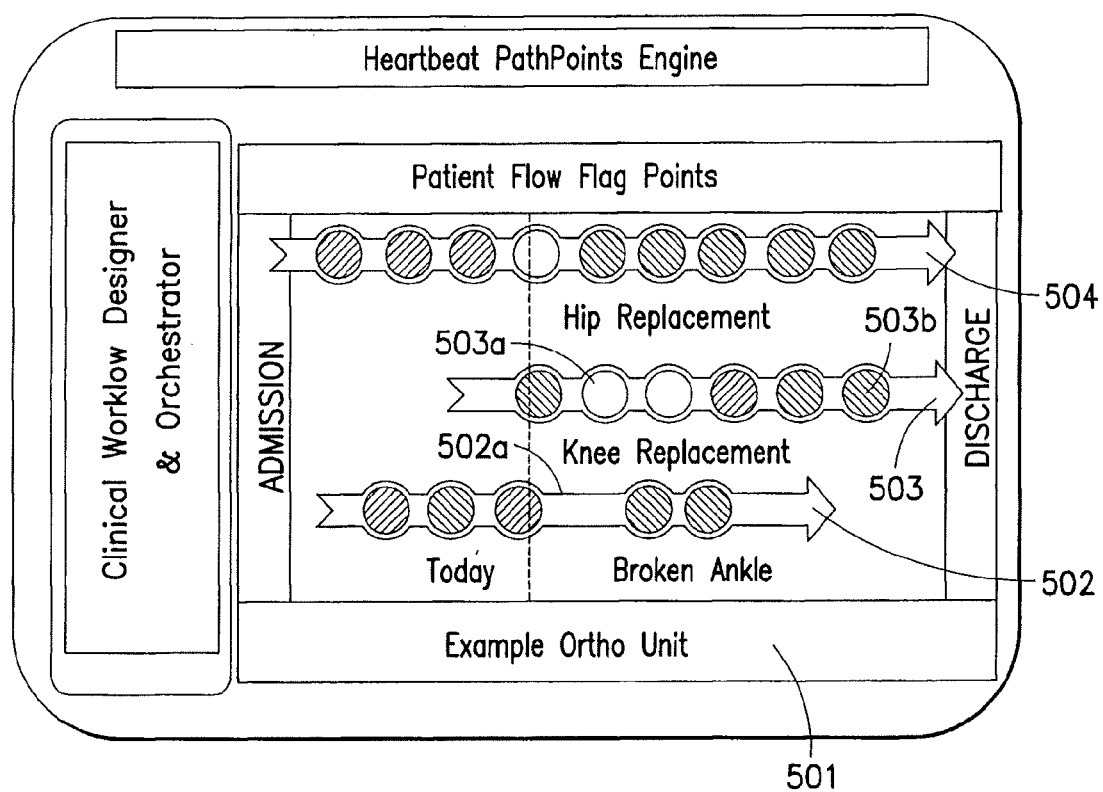
FIG. 5 is an exemplary conceptual representation of task points a process resource is authorized to act upon.

FIG. 5 shows an exemplary conceptual representation of task point, of a number of process pathways representations, relevant to a particular team member or unit to whom the task points are relevant. The exemplary embodiment illustrated in FIG. 5 shows, for instance, the task points for an orthopedic unit 501. For example, multiple patients may be assigned to the orthopedic unit 501 for various tasks, for instance, a hip replacement 504, a knee replacement 503 and a broken ankle 502. Each patient may, for instance have multiple task points corresponding to the process pathway of each job generated for said patient. In an exemplary embodiment, a team member within the orthopedic unit, for example, may only be sent (for example to their mobile device(s) 16 as described previously) task points relevant to the orthopedic unit. In the exemplary embodiment, the task points for the patient with a broken leg 502 relevant to an orthopedic unit may mean that some of the total task points for the patient with a broken leg corresponding to that patient's process pathway may not be sent to the orthopedic unit because they are not relevant to the orthopedic unit. In FIG. 5, for instance, this may be illustrated in that exemplary embodiment, as a gap 502a on the list of task points for that patient. In alternate embodiments, this may be done in any suitable alternative fashion. In an exemplary embodiment, the task point or its representative notification, relevant to a particular unit may also indicate state of such a task point.

For instance, task point 503a and 503b for the task point list for the patient getting a knee replacement 503 have different states, for example represented in FIG. 5 as having different colors. In alternate embodiments, any suitable means of representing states of task points relevant for a relevant team member may be used.

Figure 7:
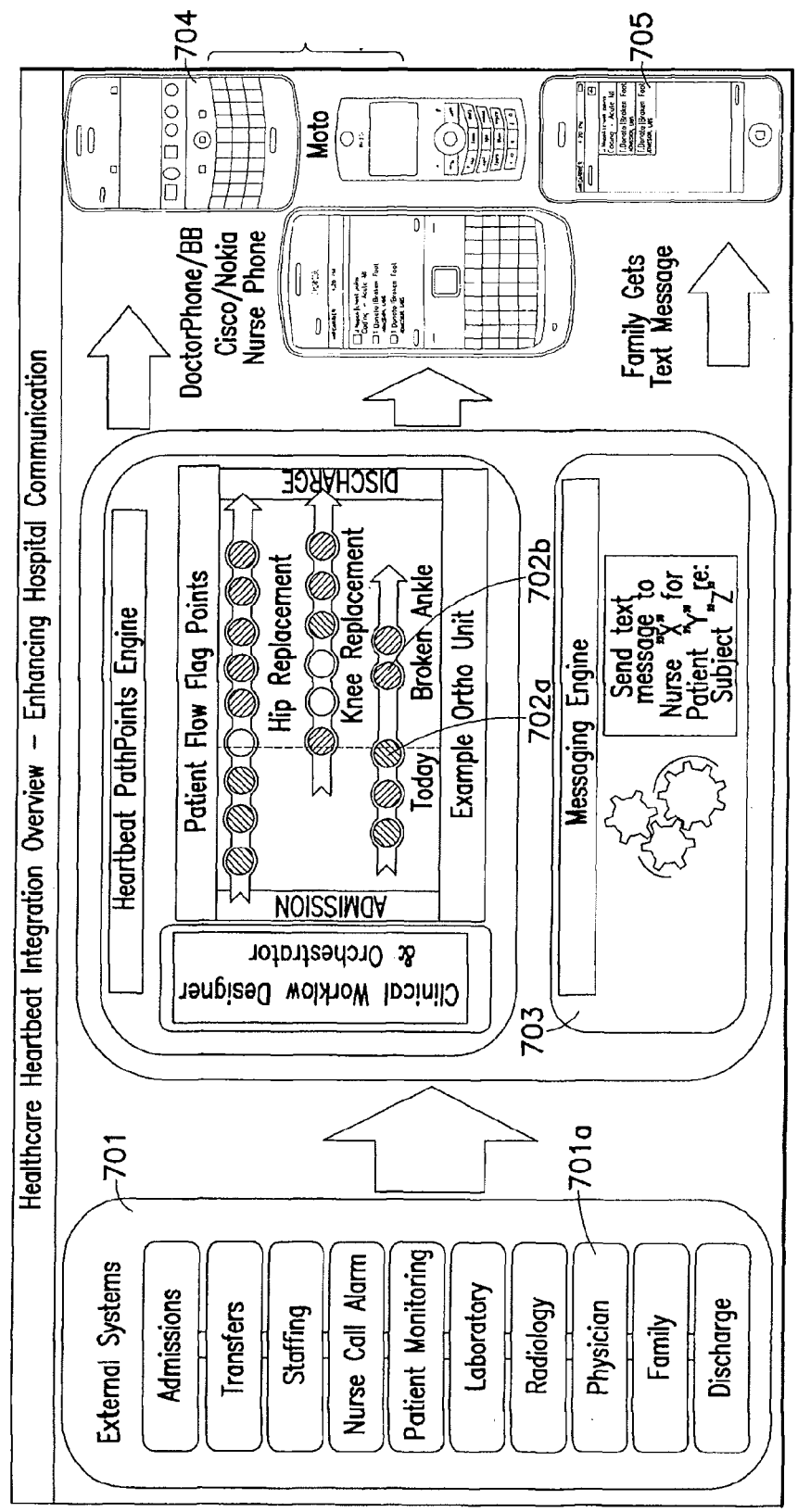
FIG. 7 is an exemplary conceptual diagram of an enhanced communications system in accordance with the exemplary embodiment.

FIG. 7 shows an enhanced communications system for a process pathway system. The process pathway system may allow for a simplified enhanced communications system integrated with the process pathway system, allowing for maximum efficiency. For example, in a healthcare context, an average healthcare provider walks between 4 and 5 miles per shift. Much of the time, communications may not be optimal. For example, within the healthcare context, a doctor treating a patient may not know precisely who to contact regarding a certain aspect of a patient's treatment. Time and effort may be expended in determining the parties that must be reached, putting the patient's health at risk. In the exemplary embodiment illustrated in FIG. 7, an integrated messaging system is disclosed. A series of external systems 701 which may generate messages are shown in the exemplary embodiment. These external systems may correspond to entities or units within the work flow environment associated with task points as described previously for instance, Admissions, Transfers, Staffing, Nurse Call Alarms, Patient Monitoring, Laboratory, Radiology, Physicians, Family, or Discharge within a healthcare context. In alternate embodiments, any other suitable external systems in any suitable context which may generate messages may also be included. A message request from the external systems 701 may use the process pathway system in order to generate the message in a simplified manner. In one exemplary embodiment, the task points corresponding to a job's (patient's) process pathway may be used to simplify communication. For instance, a task point for a patient process pathway may be associated or assigned to a particular team member or user. For instance, the task point 702b for a user with a broken ankle may be assigned to a particular nurse within an orthopedic unit. Because of the association of a relevant team member or user with the particular task point simplifies messaging to the relevant team member or user for a particular task point. In a non-limiting example, if an external system 701, for instance, a physician 701a, needs to contact the relevant party in regards for a particular task point 702b for a particular patient with a broken ankle. The physician may, in an exemplary embodiment, use the messaging engine 703 to generate a message to the relevant party for said task point 702b. The messaging engine 703 may, may recognize that the physician 701a needs to contact the relevant party, for example a nurse, for the task point 702. The messaging engine 703 may allow for the creation of a communication to the relevant nurse associated with task point 702b for the particular patient with the broken ankle in regards to task point 702b. The communication set up by the messaging engine 703 may then subsequently route the message to the appropriate mobile devices 704, 705. As noted, the system is platform agnostic and may be used with any suitable type of mobile devices. In this exemplary embodiment, communication may occur invisibly to the user. This may mean that the physician 701a need not know precisely who is in charge of task point 702b for that particular patient. In this exemplary embodiment, a physician 701a may only initiate a message in relation to task point 702b. The exemplary embodiment illustrated in FIG. 7 is a text message. However, in alternate embodiments, the messaging system 703 may be used for voice calls, emails, instant messaging, or any other suitable means of communication. In an exemplary embodiment, the messaging engine 703 may also determine multiple relevant parties to contact for a task point beyond the user or team member associated with that task point. For example, a messaging engine 703, upon failure to reach a particular party associated with a task point may, in one exemplary embodiment, attempt to contact other parties within the same unit, or the unavailable relevant party's supervisor, or in alternate embodiments, any suitably relevant person that may be contacted in connection with that particular task point. In yet alternate embodiments, other types of messaging may also be sent with the messaging system 703. For instance, alerts, such as patient monitor alerts, acute status alerts, nurse call alerts, laboratory alerts, or any other similar types of alerts may all be sent from their respective external systems to alert relevant parties associated with a particular task point. Messaging engine 703 may also, in another exemplary embodiment, allow the communication of other information, such as, but is not limited to, laboratory results or radiology results. In alternate embodiments, any suitable form of messaging may be sent with the messaging engine.

Figure 8:
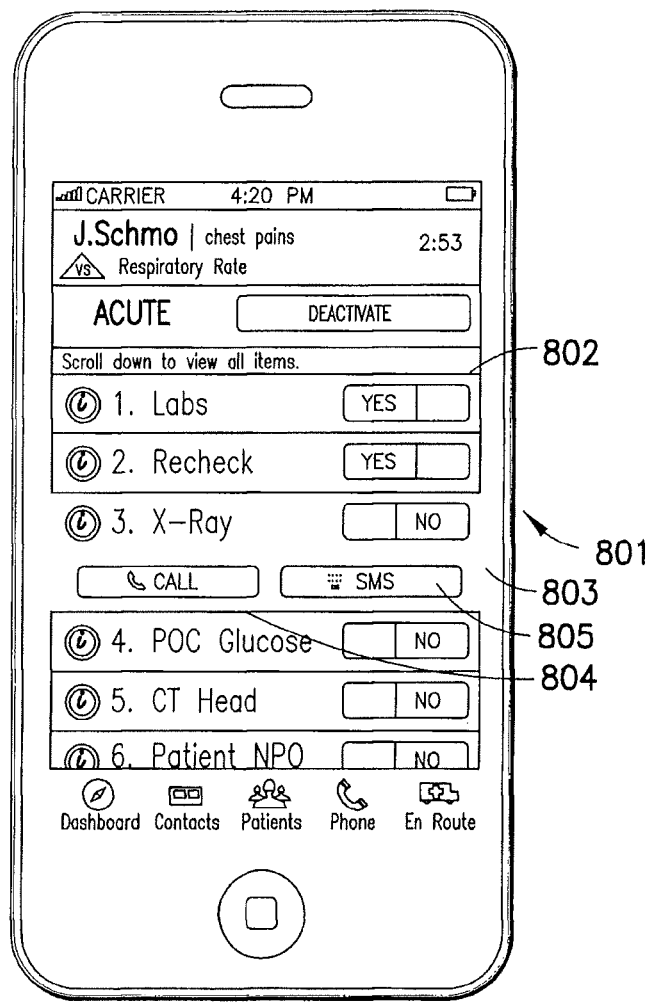
FIG. 8 is an exemplary user interface for an enhanced communications system in accordance with the exemplary embodiment.
Figure 8A:
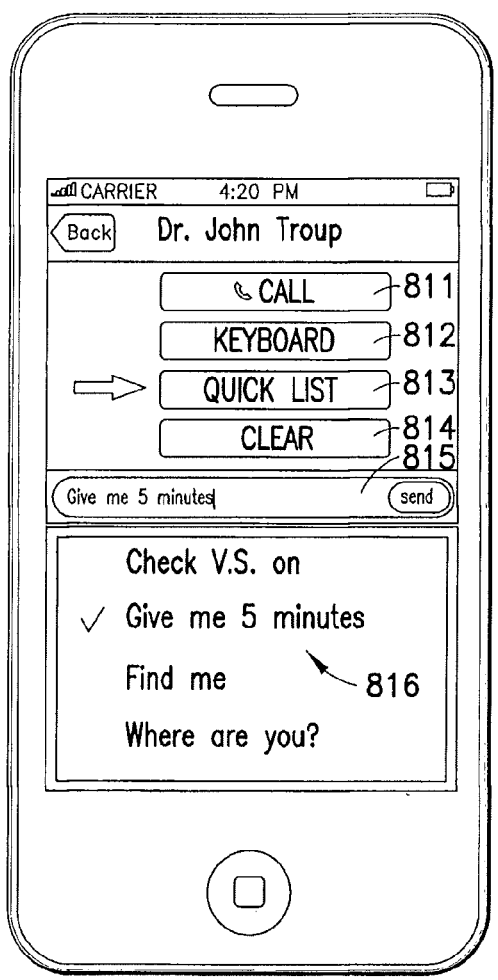
FIG. 8A is another exemplary user interface for an enhanced communications system.

FIG. 8 illustrates an exemplary embodiment of how simplified communications may be set up on a representative mobile interface. An exemplary embodiment of a user interface 801 is shown with a representation of an exemplary process pathway for a patient currently experiencing acute chest pains. Multiple task points 802 are shown within the user interface, representing the task points within the user's process pathway and their current conditions. A single task point item 803 is currently highlighted within the user interface, the highlighted task point regarding a task point for X-Ray. The highlighted task point 803 presents two possible communications options to a user. The user may either choose option 804, which would allow for the establishment of a voice communication in relation to the highlighted task point 803. The user may also have the option of selecting the option for an SMS messaging 805 in relation to the highlighted task point. In alternate embodiments, any other suitable form of communications in relation to a task point may also be presented. If the user selects option for SMS message 805, the user may be presented with the exemplary user interface illustrated in FIG. 8A. FIG. 8A illustrates an exemplary embodiment of a simplified SMS messaging function. In an exemplary embodiment, the selection of the SMS option 805 may not require the user to know the relevant party to contact in relation to the highlighted task point 803. However, the system may automatically determine the relevant party to contact, in the example cited, Dr. John Troup. The process of selecting the relevant party to contact may be invisible to the user and allows the system to allow the user to always contact the most relevant party for a particular task point. In an exemplary embodiment, this may be done by associating a task point with one or more relevant parties—for example, relevant parties who are assigned to perform the task point or any other suitable parties. In alternate embodiments, selection of relevant parties may be by any other suitable means, for example, looking at the context of the task point and dynamically determining the most relevant available contact, or any other relevant contacts. In alternate embodiments, the relevant party selected for a communication may not just be a single individual as seen in FIG. 8A. The system may also select multiple individuals for contacting, such as, but not limited to, contacting a unit, supervising personnel, or any other suitable groups of relevant parties.

Figure 8B:
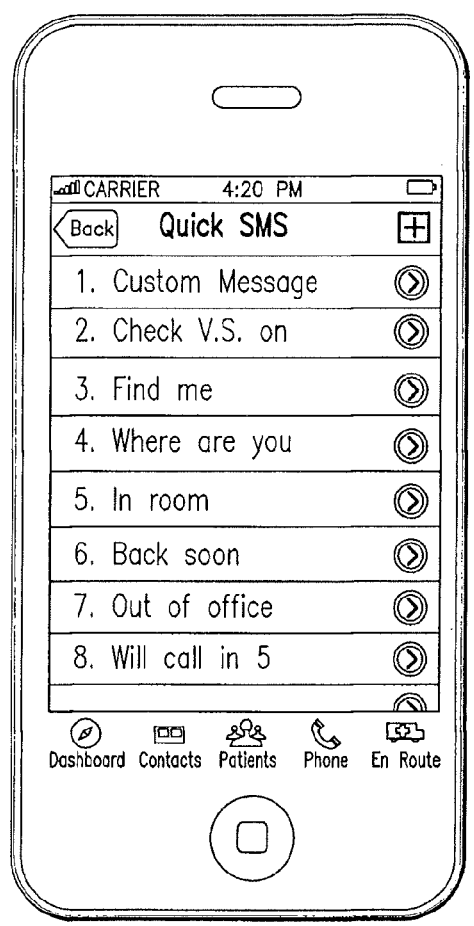
FIG. 8B is still another exemplary user interface for an enhanced communications system.

Referring again to FIG. 8A, the simplified SMS options may present a user with multiple exemplary options. The user may be presented with the option to call the relevant contact 811 instead of creating a SMS message. The user may also be given an option to generate a customized text message with a keyboard option 812 and composed in the text bar 815 before it is sent. Alternately, to quickly respond to a text message, the user may have the option to call up a quick list of predefined responses 813 and to select a predefined response from the quick list 816 to be sent instead of constructing a custom text message. In an exemplary embodiment, this quick list may be user defined (see FIG. 8B), or in alternate embodiments, they may be system defined, or in yet other possible embodiments, any suitable means for defining such a quick list may be possible. This is, again, sent via the text bar 815. In alternate embodiments, any options for communications may be presented for any suitable form of communication. For example, a voice call may give a user an option to establish a voice call, to send a message to voice mail, or to page a person over a PA system, or any other suitable options.

Referring now to FIG. 6, an exemplary embodiment illustrating a list of jobs being processed by system 10 (see also FIG. 1) such as patients 601 within a medical context is shown. The list of patients 601 may be, in an exemplary embodiment, a list of a team member's task points. In alternate embodiments, the list of patients 601 may be used for any other suitable purpose. The list of patients 601 may include indicators for alerts and messages. For example, the presence of an phone icon 602 may indicate that a message related to the associated patient is present. Specifically, multiple types of messages may be indicated, such as, in the exemplary embodiment a voice message 603 or an SMS message 602. In alternate embodiments, any other suitable messages may be indicated. FIG. 6 also illustrates an exemplary embodiment of indicators for patients. For example, a VS within a triangle 606 may indicate a vital sign exception! indicator for said patient, while an "A!" within a triangle 605 may indicate that a patient's condition is acute. These may, in alternate embodiments, take any form of suitable indicators, including in a nonlimiting example, the presence of clinical data, or any other suitable information and may be configurable according to the needs of an organization. These indicators may, in an exemplary embodiment, be messages, or in an alternate embodiment, a notification sent from the system backend or any alternate suitable implementation. In yet alternate embodiments, any sort of suitable message may be presented, for instance, in a nonlimiting example, messages of delays on the execution of tasks sent to supervisors generated by the system backend, or any other sort of messages.

Alternate embodiments may also have other functionality. In one exemplary embodiment, for quality control measures may be available to the system. For example, within a healthcare context, efficiency and proper satisfaction of procedure may be necessary. Failure to maintain proper quality control measures may result in reduced efficiency or injury to patients. This may be especially true for particularly serious problems. Within a healthcare context, for instance, patients with conditions such as strokes, pneumonia, chest pains and other similar high priority problems may require quality mandated measures to ensure that proper care is given. The system may, in one exemplary embodiment, be capable of tracking task points and protocols and any state changes as described above, for example, by time stamping or recording instances of occurrence. In alternate embodiments, any sort of information may be tracked within the system to create a traceable record of actions done as part of an auditable record. For example, call records may be recorded and time stamped, or when task points are completed, or when any delays occur or vital sign information. In alternate embodiments, any sort of information may be recorded and tracked by the system in creating an record that may be audited.

Figure 9:
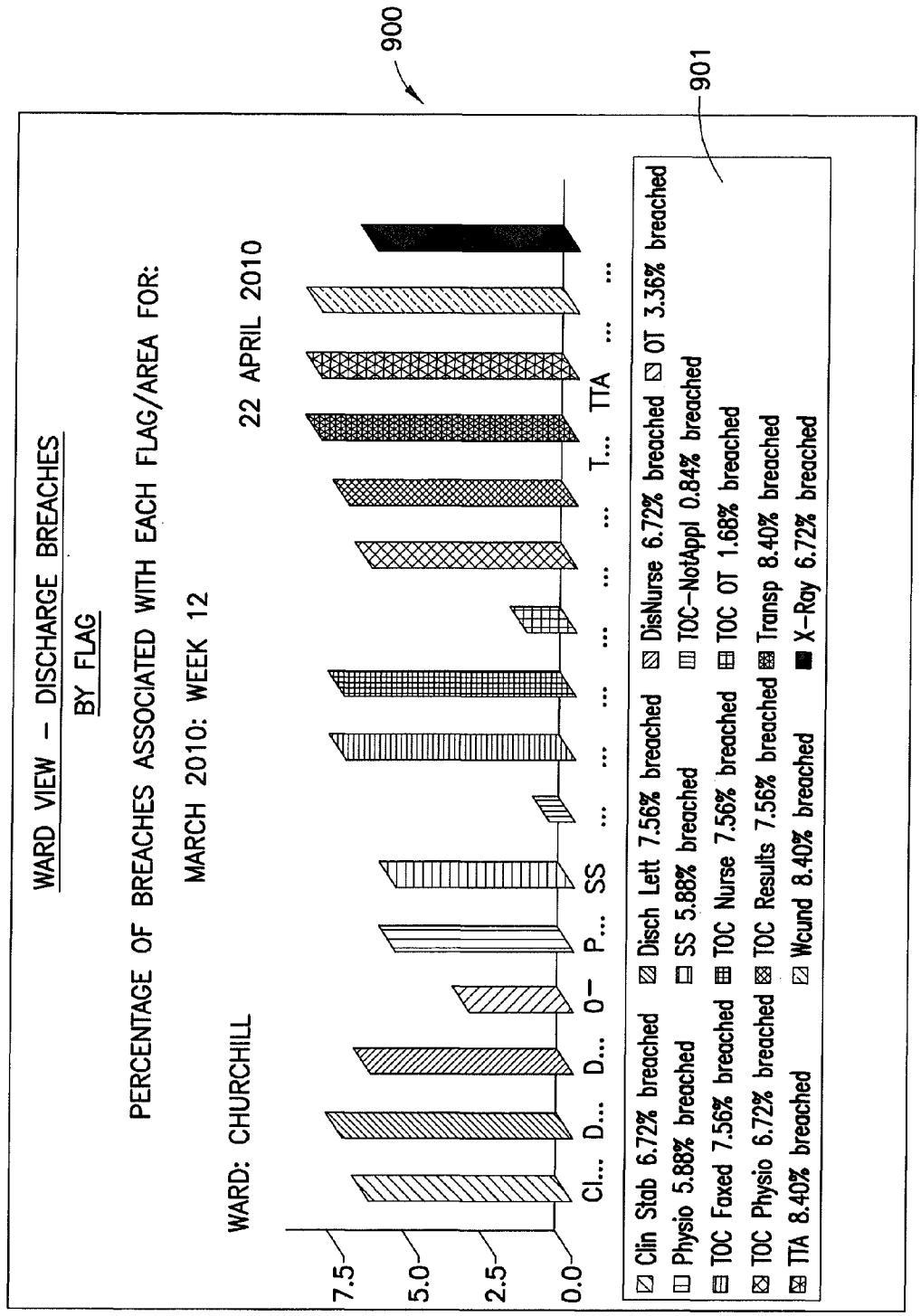
FIG. 9 is an exemplary auditing report as generated by the system.

FIG. 9 represents an exemplary embodiment of a possible report for auditing purposes. FIG. 9 illustrates an exemplary report where a graph 900 as may be realized the report may have any desired configuration or representation and its associated legend 901 may illustrate the number of times a breach of process protocols generated by the system may occur. These may included, in an exemplary embodiment, possible delays, errors, miscommunications, or failure to follow the prescribed tasks according to the process pathways generated for patients, or any other suitable breaches of procedure or rules within the system. In alternate embodiments, any suitable information that may be tracked, or time-stamped, or recorded by the system, or any other suitable information may be used for the generation of a report. In yet alternate embodiments, users may define the format and data used for a report, or the system may have predefined reports, or in other embodiments, any suitable combination thereof. In alternate embodiments, audit records may be in other forms. For example, an audit record may not be simply limited to a patient within a medical context, but also for a unit of team members, or for hospital-wide actions, or any other useful information about the flow of operations within a system. Reporting for any auditing or tracking information may also be reported in the form of, for example, clinical scores or efficiency scores, such as, for example, NIH Stroke scales or Timmi scores, or any other suitable measure. In an exemplary embodiment, auditing may be retroactive—any reporting is generated after the action occurred. In alternate embodiment, real time or prospective quality control may also be available. For instance, for high risk patients within a medical context, breaches of mandated quality control procedures may be monitored and reported to relevant parties as they occur. In alternate embodiments, any other suitable form of auditing reporting may also be used.

Another aspect of the exemplary embodiment may be a system for the administration of the system backend. Referring now to FIG. 11, in an exemplary embodiment of the system 1100, this may be done through the means of a client device 1101 capable of accessing the system backend's 1102 administrative operations and settings (i.e. rules or procedures or criteria necessary to generate a process pathway) via a simplified user interface 1105 (an example of an exemplary simplified user interface 1105 can be seen in FIG. 10). Thus, the client device 1101 is able to view and alter the criteria 1104 upon which the process pathway may be generated and controlled. The system backend 1102 may, in one exemplary embodiment, be the same or a part of the system backend 11 as seen on FIG. 1. In alternate embodiments, the system backend 1102 may refer to any other suitable device. In another exemplary embodiment, the client device may be, in one embodiment, a mobile device 16 as seen on FIG. 1, but may in alternate embodiments, be any other suitable client device such, as, for example, a computer terminal, or a part of the system backend 1102, or any other suitable client device. A simplified user interface 1105 is one such that allows lay individuals to make modifications to the administration of the backend without knowledge of programming, scripting, or other advanced means to extend or alter the functionality of existing systems as is often the case in the present art. This may be done, for instance, via a web-based interface. In alternate embodiments, this may also be done by means of an application with a simplified user interface 1105, or any other suitable means. In another exemplary embodiment, the simplified user interface 1105 may require reduced input—allowing users to create alterations within the system with a one-step action (for example, toggling rules to apply) or to create additional or edit additional criteria by means of inputting and selecting simple rules within a simplified user interface to construct criteria. In an exemplary embodiment, the simplified user interface may allow a user to control various aspects related to various operations within a system backend. For instance, a user may be able to define, on the fly, rules for generating process pathways within a system backend 1104. These would allow a user to be able to modify the predefined rules used to generate process pathways within the system backend 1104. The user may, in an exemplary embodiment, add, edit, or remove any rules within the system. In alternate embodiments, any other changes to the rules may be made. In another exemplary embodiment, users may also modify process pathways generated by the system. For example, users may add additional task points, or remove additional task points, change statuses of task points, inactivate task points, or any other suitable operation within a process pathway. In alternate embodiments, users may be able to administrate users, resources, roles, phones, or any other suitable abstract entities or rules within the system backend. In yet another alternate embodiment, the user may also extend functionality of the system backend, for example, through third-party software, or through additional rules generation, or through plug-ins, or through any other suitable means to extend functionality of the system backend. In an exemplary embodiment, the changes in any criteria upon which a system backend 1104 uses to generate process pathways may result, for instance, updates of any existing process pathways dynamically. In such a situation, any future process pathways may conform to the updated criteria. In alternate embodiments, no changes to any existing process pathways may occur if, for instance, the changes to the criteria do not affect any existing pathways, or any other suitable reason. In an exemplary embodiment, after the updating of any existing process pathways, the system may generate an additional series of task points to correspond to the updated process pathways which are then sent to mobile devices 1103. In alternate embodiments, the system may also perform any other suitable action in response to the updating of process pathways.

Figure 10:
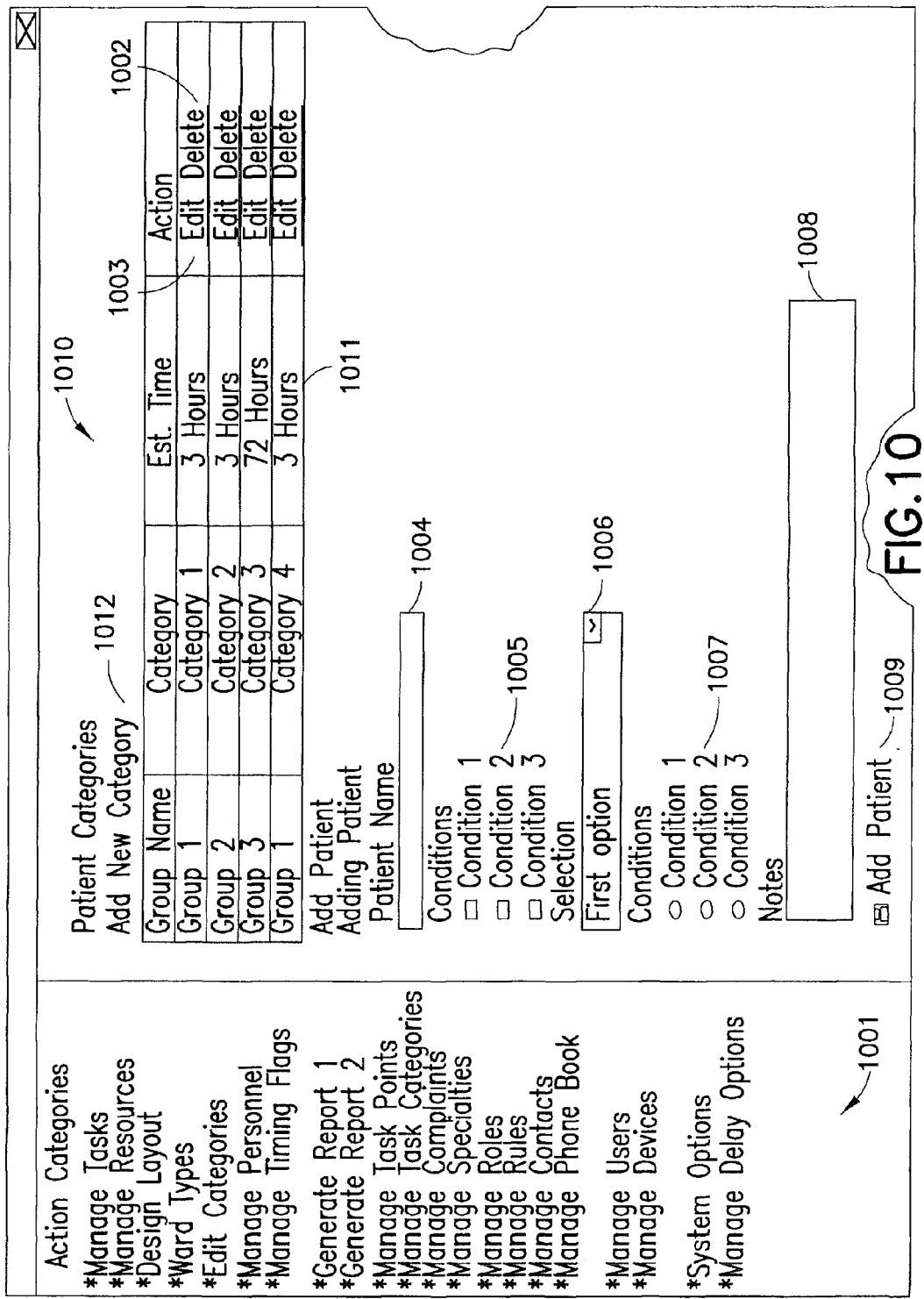
FIG. 10 is an exemplary user interface for a client device viewing and selecting criteria on a system backend.
Figure 11:
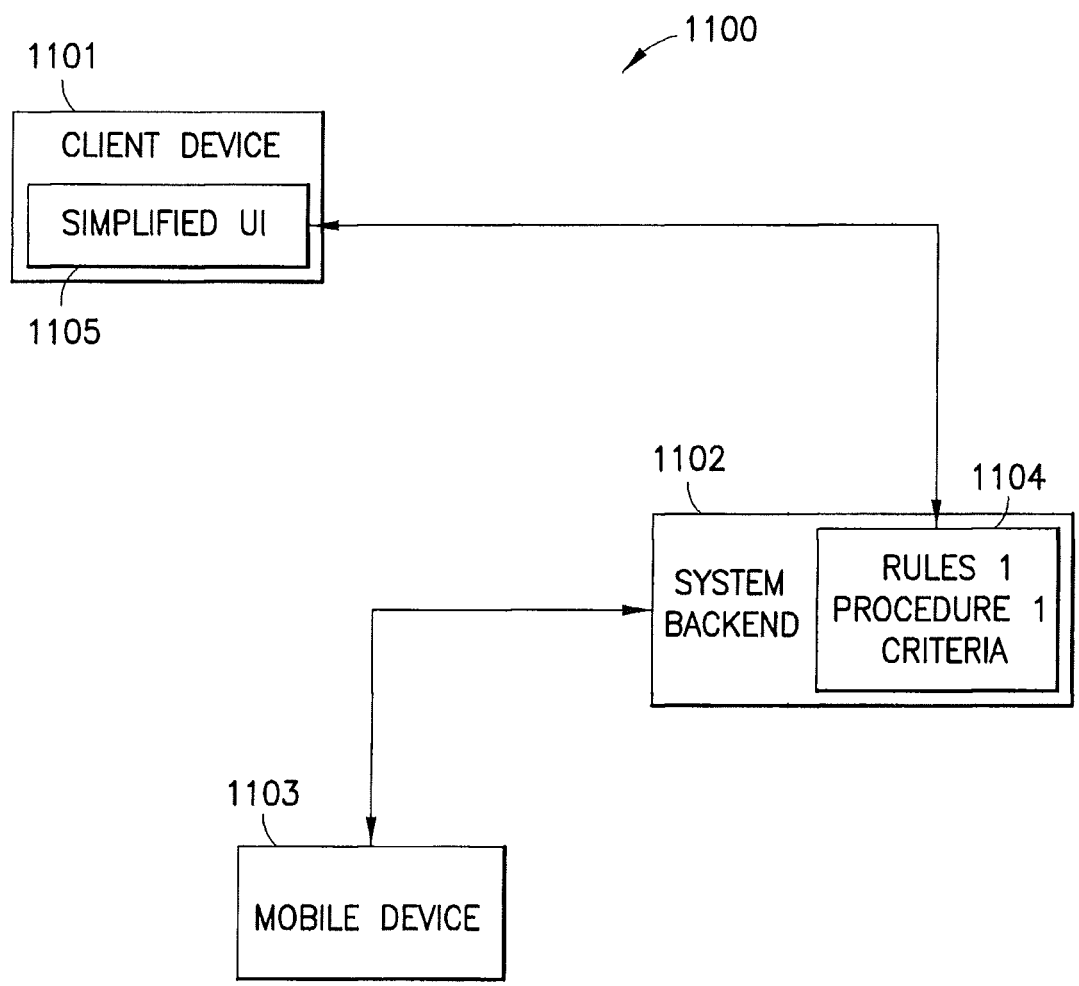
FIG. 11 is an exemplary schematic diagram of a system for viewing and selecting criteria on a system backend.

FIG. 10 is an exemplary user interface for a client device accessing the backend's administrative settings and operations. The exemplary user interface is for illustrative purposes only and may taken the form of any suitable user interface which may represent a simplified method of accessing, viewing and selecting the backend's administrative settings and operations. In an exemplary embodiment, there may be a set of categories 1001 of settings which may be selected and viewed by a user. These may include, for instance, action categories that allows users to edit categories within the system, or to manage tasks, to edit timing flags, edit roles, edit rules, edit contacts, edit users, or any other suitable criteria underlying a system backend's administrative settings and operations. In alternate embodiments, these may allow a user to alter the process protocols directly within a system. In yet alternate embodiments, any other suitable action categories may also be included, including management of sensor/vital sign devices, or integration with third party software, or any other suitable action category. The exemplary user interface also has a portion 1010 that may, for instance, be used to viewing and selecting or modifying settings after selecting an action category, or any other suitable means of altering settings, rules and criteria within the system backend. These may take multiple forms. For example, the information may be presented to a user, in the exemplary example, with a listing of information 1011 which the users have the option to act upon. In this current exemplary embodiment, a user may be able to edit a category 1003, delete a category 1002 or add a new category 1012. In yet alternate embodiments, any other suitable actions may be available. In some embodiments, the action may be one-step, for example the delete function 1002. In embodiments, the action may be multi-stepped but simplified. For example, an option to add a patient may allow for multiple types of inputs (i.e. a multi-stepped action). Information may be inputted by a user by means of any suitable forms of text boxes 1004, 1008, check boxes 1005, drop down selections 1006, and radio buttons 1007, and buttons 1009 for means to enter information. In alternate embodiments, any other method for inputting information may be used, for instance, uploading images, or importing data from other applications, or any other suitable means. In all cases, the information input is simplified—i.e. does not require the need for programming to extend the functionality or settings of the system, or require any technical depth. Rather, in one embodiment, a lay person can edit and make changes to the system settings. As shown, these may be, in one embodiment, similar to the forms as shown. In alternate embodiments, they may be a series of toggles, or a simplified logic statement generator, or a GUI-based database manager, or any other suitable means. In yet alternate embodiments, the client user interface may take any suitable embodiment for the simplified means of managing the administrative settings and operations of the system backend.

Figure 3A:
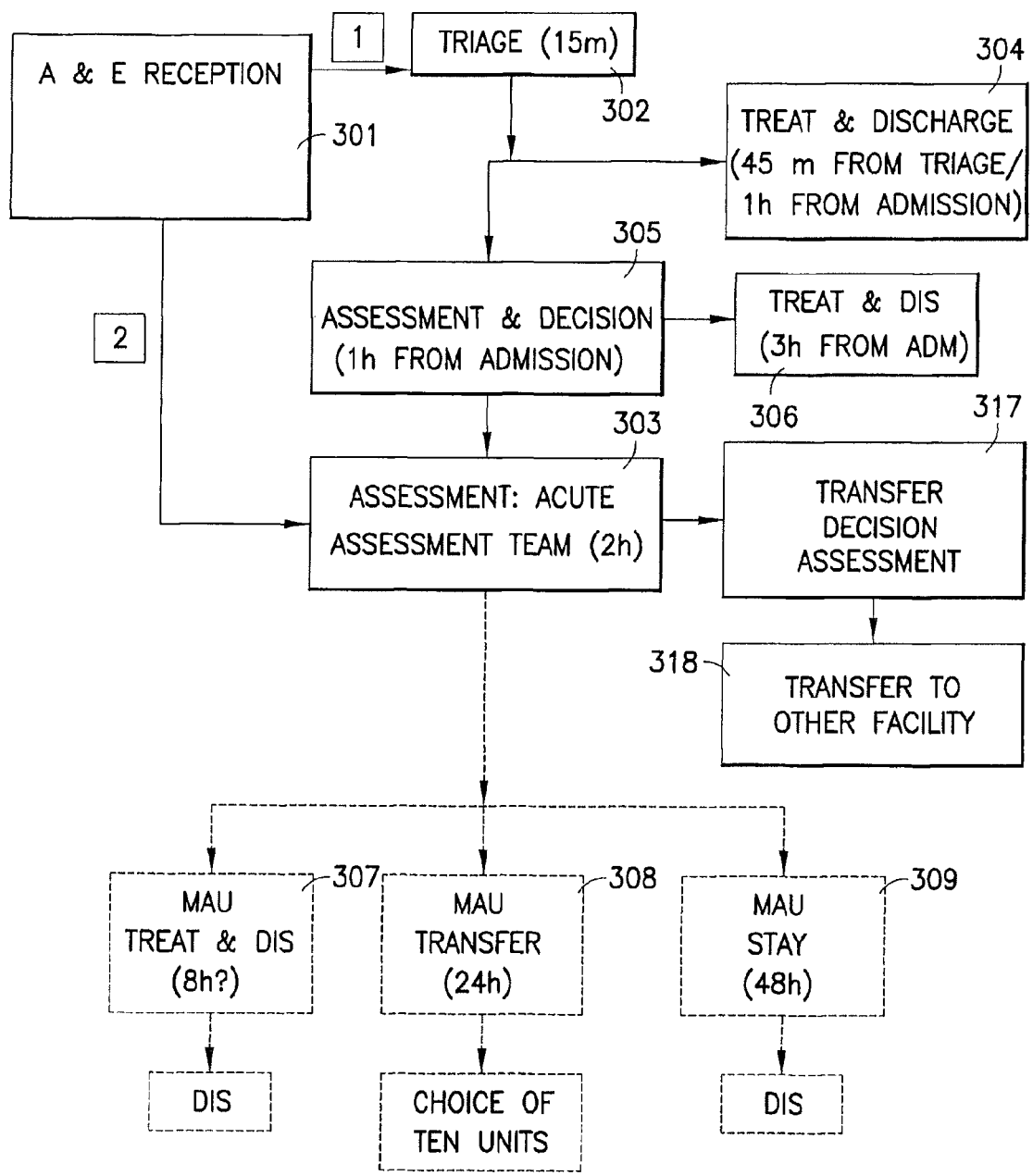
FIG. 3A is an exemplary flow diagram illustrating a possible set of changed rules and procedures used in a process pathway generation system.

Referring now to FIG. 3A, an exemplary illustration of a change in the rules for the generation of a process pathway is illustrated. In an exemplary embodiment, this change may be, for example, due to a change of the rules and procedures from which a process protocol may be generated by a client accessing a system backend as seen with FIG. 10 and as previously noted. In alternate embodiments, such a change in the rules and procedures for the generation of a process pathway can be done by any suitable means by which the rules and procedures may be changed, including, but not limited to, automatic optimization by the system backend, or rule updates from an external source, or any other suitable means. As seen previously in FIG. 3, and now seen on FIG. 3A, an exemplary set of rules and procedure may be presented. Blocks 301-309 all correspond to the exemplary embodiment of a set of rules for the generation of a process pathway as seen in FIG. 3. Blocks 307, 308 and 309 are shown in dash-lines may indicate a possible change within the exemplary set of rules and procedures. In an exemplary embodiment, these may be removed or disabled by a user accessing the system backend administrative settings and operations via a client interface as seen in FIG. 10. In the exemplary embodiment of the rules and procedure as seen in FIG. 3A, these no longer are possible as potential task points within a process pathway. In the exemplary embodiment, additional rules and procedures, which may be represented by the darkened arrowed lines and the darkened boxes 317 and 318 may be seen. These may be, for instance, additional rules and procedures that may be added by a user accessing the system backend administrative settings and operations via a client interface as seen in FIG. 10. These may result, for instance, additional potential task points, or in alternate embodiments, any other suitable consequences. An example of additional task points as the result of changed rules or procedures can be see in FIG. 2, where the series of potential task points/notifications 216 may correspond to the suitable consequences of changes to the rules and procedure. In alternate embodiments, any suitable means by which additional rules and procedures may be added may be used. In yet alternate embodiments, changes within a set of rules and procedures from which a process protocol may be generated may be changed by any suitable means, for any suitable purpose. For instance, the rules and procedures may be edited, or attributes for specific rules and procedures may be altered, or rules and procedures may be rearranged, or default states for rules and procedures may be changed, or any other suitable means of altering said rules and procedures. The changed rules and procedures may be used, in one exemplary embodiment, to alter a generated process pathway from one set of notifications or task points to a second set of notifications or task points where in there is at least some difference between the first and second set of notifications or task points. In alternate embodiments, no changes to a generated process pathway may took place, or any other suitable results of the modification of the set of rules and procedures may result.

Alternate embodiments, additional functionality may be present. In one possible embodiment, the system may further be connected or integrated with clinical data within a healthcare context to alert users to clinical data as they arrive. This may, for instance, prevent delay for a clinical data that may be available at a workstation but is unknown to a user for a particular patient. In alternate embodiments, clinical data and results (for example, but not limited to, X-ray, or blood tests, or CAT scan results) may be delivered to a user's mobile device directly and timing the healthcare provider response and or acknowledgement of said result. In yet alternate embodiments, any possible level of integration with clinical data may be available.

In another possible embodiment, the system may allow users to log in to the system from their mobile devices through a secured login setup.

In another possible embodiment, the system may be integrated with third party systems, such as, but not limited to a Hospital Information System (HIS), pharmacy systems, human resources and time keeping systems, or any other suitable system. In other contexts such as retail, any other suitable third party software systems may be integrated with the process pathway system.

In another possible embodiment, the system may be integrated with systems for nurse call monitors and vital signs monitors within a medical context. In alternate embodiments, any possible suitable monitoring system may be used.

In another possible embodiment, the system may be configured to track resources within the organization. Within a medical context, this may include, for instance, medication, the availability of beds, the availability of surgical supplies, or any other suitable resources that may be necessary for tracking. In yet alternate embodiments, any resource in any other suitable context may also be tracked.

In accordance with the exemplary embodiment, a system for controlling process pathways is provided. The system includes a network, a system backend communicable with said network comprising a processor configured to generate a process pathway based on a predefined set of rules reflecting a predetermined condition, and a series of notifications corresponding to the process pathway for communication over the network, at least one mobile device communicable with said system backend via said network, the at least one mobile device being configured to receive from said backend via said network at least one notification, of said series of notifications, the at least one notification defining a task of the process pathway, and upon which notification a user is authorized to act, wherein said at least one mobile device is further configured to allow said user to modify a state of said at least one notification with a one-step action, wherein said at least one mobile device is further configured to communicate the modified state of the at least one notification to the system backend over said network and wherein said modified state of the at least one notification causes said processor to effect a change to said process pathway based upon said modified state.

In accordance with the exemplary embodiment, a method for generating process pathways is provided. The method includes generating a process pathway based upon a predefined set of rules reflecting a predetermined condition on a system backend communicable with a network generating a series of notifications corresponding to said process pathway for communication over said network on said system backend, communicating at least one notification of said series of notifications, the at least one notification defining a task of the process pathway, and upon which notification a user is authorized to act to a mobile device communicable with said network from said system backend enabling said user to modify a state of the at least one notification with said mobile device in a one-step action, communicating the modified state of the at least one notification to said system backend over said network from said mobile device; and effecting a change to said process pathway within said system backend with said modified state of the at least one notification.

In accordance with the exemplary embodiment, a non-transitory computer readable medium having computer readable program code embodied therein including computer readable code is provided. When executed, the code performs, generating a process pathway based upon a predefined set of rules reflecting a predetermined condition on a system backend communicable with a network, generating a series of notifications corresponding to said process pathway for communication over said network on said system backend, communicating at least one notification of said series of notifications, the at least one notification defining a task of the process pathway, and upon which notification a user is authorized to act to a mobile device communicable with said network from said system backend, enabling said user to modify a state of the at least one notification with said mobile device in a one-step action, communicating the modified state of the at least one notification to said system backend over said network from said mobile device, and effecting a change to said process pathway within said system backend with said modified state of the at least one notification.

In accordance with the exemplary embodiment, a system for controlling a process is provided. The system includes a system backend having a processor, a network, a client device, communicable with the system backend via a network, wherein said processor is configured to generate a process pathway based upon a set of criteria, wherein said backend processor is further configured to generate a series of notifications corresponding to said process pathway for communication over said network, wherein said backend processor is configured to allow said client device to view and alter said set of criteria with a simplified action wherein said backend processor, in response to said alteration, changes said process pathway from a first pathway having a first set of pathway points to a second pathway having a second set of pathway points, at least one of said second pathway points is different from said first pathway points.

What is claimed is:

1. A system for controlling process pathways, the system comprising:
   a network;
   at least one mobile device;
   a system backend communicable with said network comprising a processor configured to generate a process pathway embodying a physical process having a predetermined end, the physical process comprising a series of physical tasks based on a predefined set of rules reflecting a predetermined condition and related to the predetermined end, where each physical task of the series of physical tasks corresponds to different points along the process pathway, and a series of notifications corresponding to each physical task of the process pathway for communication over the network, where the series of notifications is initiated and generated by the system backend so that the series of notifications is simultaneously displayed in real time on the at least one mobile device;
   wherein, the at least one mobile device is communicable with said system backend via said network, the at least one mobile device being configured to receive from said backend via said network the series of notifications, where the simultaneous display of the series of notifications on the at least one mobile device defines a series of corresponding progressive points along the process pathway from a process pathway generation point to the predetermined end so that the displayed series of notifications display on the at least one mobile device the series of corresponding progressive points along the process pathway, and where at least one notification of the series of notifications defines a physical task of the series of physical tasks of the process pathway and provides a user with authorization to act, and upon which notification the user is authorized to act;
   wherein said at least one mobile at least one mobile device is further configured to allow said user to modify a state of said at least one notification with a one-step action from the displayed series of notifications;
   wherein said at least one mobile device is further configured to communicate the modified state of the at least one notification to the system backend over said network; and
   wherein said modified state of the at least one notification causes said processor to effect a change to said process pathway based upon said modified state.

2. The system as claimed in claim 1, wherein the series of notifications define a process engine and configured for effecting dynamic control of the process from the at least one mobile device.

3. The system as claimed in claim 1, wherein said at least one mobile device is configured to communicate with said backend with a data application.

4. The system as claimed in claim 3, wherein said data application is configured for simplified communication.

5. The system as claimed in claim 4, wherein said data application is configured to use integrated communications for said simplified communications.

6. The system as claimed in claim 4, wherein said data application is configured to use external communications for said simplified communications.

7. The system as claimed in claim 1, wherein said processor is further configured to track activity related to the process pathway over the system.

8. The system as claimed in claim 1, wherein said processor is further configured to receive data related to clinical data.

9. The system as claimed in claim 8, wherein said processor is further configured to generate at least one clinical data notification, the at least one clinical data notification relating to availability of said clinical data, wherein said at least one clinical data notification may be communicated to the at least one mobile device via said network.

10. The system as claimed in claim 1, wherein said processor is further configured to generate at least one updated notification corresponding to said changed process pathway.

11. The system as claimed in claim 10, wherein said mobile device is further configured to receive from said backend via said network the at least one updated notification, the at least one updated notification defining an updated physical task of the series of physical tasks of the changed process pathway.

12. The system as claimed in claim 1, wherein the at least one notification defines an existing or future physical task of the series of physical tasks of the process pathway.

13. The system as claimed in claim 1, wherein said at least one notification can be sorted by said user on said at least one mobile device.

14. The system as claimed in claim 1, wherein users may access said at least one mobile device via a secured login.

15. The system as claimed in claim 1, wherein said processor is configured to receive monitoring data and further configured to generate at least one monitor notification based on said monitoring data to be sent to at least one mobile device.

16. The system as claimed in claim 1, wherein said at least one mobile device is further configured to allow said user to modify said state of said at least one notification to indicate delay.

17. The system as claimed in claim 1, wherein said at least one notification includes a time frame information for an authorized use action, said notification defining said physical task of the series of physical tasks of the process pathway.

18. The system as claimed in claim 1, wherein said processor may further be configured to track availability of at least one resource.

19. The system as claimed in claim 1, wherein said processor may further be configured to interact, with a third-party application.

20. The system as claimed in claim 1, wherein said at least one notification is updated in real time.

21. The system as claimed in claim 1, wherein system may further be configured to integrate imaging capabilities.

22. The system as claimed in claim 7, wherein said tracked activity may be compiled for reporting by said processor.

23. A method for generating process pathways, the method comprising:
   generating a process pathway embodying a physical process having a predetermined end, the physical process comprising a series of physical tasks based upon a predefined set of rules reflecting a predetermined condition and related to the predetermined end on a system backend communicable with a network, where each physical task of the series of physical tasks corresponds to different points along the process pathway;

initiating and generating a series of notifications corresponding to said process pathway for communication over said network on said system backend, where the series of notifications is generated so that the series of notifications is simultaneously displayed in real time on at least one mobile device;

communicating the series of notification to the at least one mobile device, where simultaneously displaying the series of notifications on the at least one mobile device defines a series of corresponding progressive points along the process pathway from a process pathway generation point to the predetermined end so that the displayed series of notifications display on the at least one mobile device the series of corresponding progressive points along the process pathway, and where at least one notification of the series of notifications defining a physical task of the series of physical tasks of the process pathway and provides a user with authorization to act, and upon which notification the user is authorized to act to the at least one mobile device communicable with said network from said system backend;

enabling said user to modify a state of the at least one notification with said at least one mobile device in a one-step action from the displayed series of notifications;

communicating the modified state of the at least one notification to said system backend over said network from said at least one mobile device; and effecting a change to said process pathway within said system backend with said modified state of the at least one notification.

24. A non-transitory computer readable medium having computer readable program code embodied therein comprising computer readable code that, when executed, performs:

generating a process pathway embodying a physical process having a predetermined end, the physical process comprising a series of physical tasks based upon a predefined set of rules reflecting a predetermined condition and related to the predetermined end on a system backend communicable with a network; where each physical task of the series of physical tasks corresponds to different points along the process pathway;

initiating and generating a series of notifications corresponding to said process pathway for communication over said network on said system backend, where the series of notifications is generated so that the series of notification is simultaneously displayed in real time on at least on mobile device;

communicating the series of notifications to the at least one mobile device, where simultaneously displaying the series of notifications on the at least one mobile device defines a series of corresponding progressive points along the process pathway from a process pathway generation point to the predetermined end so that the displayed series of notifications display on the at least one mobile device the series of corresponding progressive points along the process pathway, and where at least one notification of the series of notifications defining a physical task of the series of the series of physical tasks of the process pathway and provides a user with authorization to act, and upon which notification the user is authorized to act to the at least one mobile device communicable with said network from said system backend;

enabling said user to modify a state of the at least one notification with said at least one mobile device in a one-step action from the displayed series of notifications;

communicating the modified state of the at least one notification to said system backend over said network from said at least one mobile device; and effecting a change to said process pathway within said system backend with said modified state of the at least one notification.

25. A system for controlling a process, the system comprising:

a system backend having a processor;

a network;

a client device, communicable with the system backend via a network;

wherein said processor is configured to generate a process pathway embodying a physical process having a predetermined end, the physical process comprising a series of physical tasks based upon a set of criteria and related to the predetermined end, where each physical task of the series of physical tasks corresponds to different points along the process pathway;

wherein said backend processor is further configured to generate a series of notifications corresponding to said process pathway for communication over said network, where the series of notifications is initiated and generated by the system backend so that the series of notifications is simultaneously displayed in real time on the client device, and where the simultaneous display of the series of notifications on the client device defines a series of corresponding progressive points along the process pathway from a process pathway generation point to the predetermined end so that the displayed series of notifications display on the at least one mobile device the series of corresponding progressive points along the process pathway;

wherein said backend processor is configured to allow said client device to view and alter said set of criteria with a simplified action from the displayed series of notifications;

wherein said backend processor, in response to said alteration, changes said process pathway from a first pathway having a first set of pathway points to a second pathway having a second set of pathway points, at least one of said second pathway points is different from said first pathway points.

26. The system as claimed in claim 25, wherein said backend processor initiates and generates a second series of notifications corresponding to said second pathway so that the second series of notifications are simultaneously displayed in real time on the client device.

27. The system as claimed in claim 25, wherein said simplified action may be a one-step action.

28. The system as claimed in claim 25, wherein said backend processor is configured to allow said client device to view and alter available process pathways with a simplified action.

29. The system as claimed in claim 25, wherein said backend processor is configured to allow said client device to view and alter a category of path points with a simplified action.

30. The system as claimed in claim 25, wherein said backend processor is configured to allow said client device to view and alter a quality measure rule with a simplified action.

31. The system as claimed in claim 25, wherein said backend processor is configured to allow said client device to view and alter a role with a simplified action.

32. The system as claimed in claim 25, wherein said backend processor is configured to allow said client device to view and alter a patient type with a simplified action.

33. The system as claimed in claim 25, wherein said client device is a part of said system backend.

* * * * *

UNITED STATES PATENT AND TRADEMARK OFFICE
CERTIFICATE OF CORRECTION

PATENT NO. : 9,760,682 B2  
APPLICATION NO. : 13/027158  
DATED : September 12, 2017  
INVENTOR(S) : Mark Page 1 of 1

It is certified that error appears in the above-identified patent and that said Letters Patent is hereby corrected as shown below:

On the Title Page

Item (12) replace "Mark" with --Mark et al.--.

Item (72) Inventor, should read:  
--Jacob Mark, Needham, MA (US); James Edward Charles Webb, San Francisco, CA (US)--.

Signed and Sealed this  
Sixteenth Day of April, 2019

Andrei Iancu  
*Director of the United States Patent and Trademark Office*